(12) United States Patent
Nauwelaers et al.

(10) Patent No.: US 8,409,803 B2
(45) Date of Patent: *Apr. 2, 2013

(54) RESPIRATORY SYNCYTIAL VIRUS (RSV) VIRAL LOAD DETECTION ASSAY

(75) Inventors: David Nauwelaers, Kortrijk-Dutsel (BE); Lieven Jozef Stuyver, Herzele (BE); Alison Velyian Todd, Glebe (AU); Elisa Mokany, Woolooware (AU); Paul Ean Young, Engadine (AU)

(73) Assignee: SpeeDX Pty Ltd., Eveleigh (AU)

( * ) Notice: Subject to any disclaimer, the term of this patent is extended or adjusted under 35 U.S.C. 154(b) by 44 days.

This patent is subject to a terminal disclaimer.

(21) Appl. No.: 12/529,577

(22) PCT Filed: Apr. 4, 2008

(86) PCT No.: PCT/EP2008/054073
§ 371 (c)(1),
(2), (4) Date: Sep. 2, 2009

(87) PCT Pub. No.: WO2008/122598
PCT Pub. Date: Oct. 16, 2008

(65) Prior Publication Data
US 2010/0221711 A1    Sep. 2, 2010

(30) Foreign Application Priority Data

Apr. 6, 2007 (EP) .................................. 07105823
May 15, 2007 (EP) .................................. 07108211

(51) Int. Cl.
*C12Q 1/68* (2006.01)
*C07H 21/04* (2006.01)

(52) U.S. Cl. .................................. 435/6.11; 536/24.32
(58) Field of Classification Search ........................ None
See application file for complete search history.

(56) References Cited

FOREIGN PATENT DOCUMENTS

| EP | 543942 B1 | 6/1993 |
| EP | 1063296 A1 | * 12/2000 |
| WO | WO-9202638 A1 | 2/1992 |
| WO | WO-2007041774 A1 | 4/2007 |

OTHER PUBLICATIONS van Woensel et al. Pediatr. Infect. Dis. J. Aug. 22, 2003 (8): 721-6.*
Buck, G. et al. "Rapid, Simple Method for Treating Clinical Specimens Containing Mycobacterium Tuberculosis to Remove DNA for Polymerase Chain Reaction", Journal of Clinical Microbiology, Washington, D.C. US, vol. 30, No. 5, May 1992, pp. 1331-1334. XP000619643.
Loens, K. et al. "Evaluation of NucliSens EasyMAG for Automated Nucleic Acid Extraction from Various Clinical Specimens", Journal of Clinical Microbiology, Feb. 2007, vol. 45, No. 2, pp. 421-425. XP002446461.
Chandler, N.M. et al. "Caspase-3 Drives Apoptosis in Pancreatic Cancer Cells after Treatment with Gemcitabine", Journal of Gastrointestinal Surgery, Quality Medical Publ., St. Louis, MO, US, vol. 8, No. 8, Dec. 1, 2004, pp. 1072-1078. XP004673133.

* cited by examiner

*Primary Examiner* — Samuel Woolwine
*Assistant Examiner* — Suchira Pande
(74) *Attorney, Agent, or Firm* — Woodcock Washburn LLP

(57) ABSTRACT

The invention concerns a method for the extraction of nucleic acids from biological samples e.g. tissue material or sputum derived from human or animal species and the quantitative detection thereafter of said nucleic acids e.g. in terms of viral load, more specifically RSV viral load detection.

6 Claims, 7 Drawing Sheets

Figure 1:
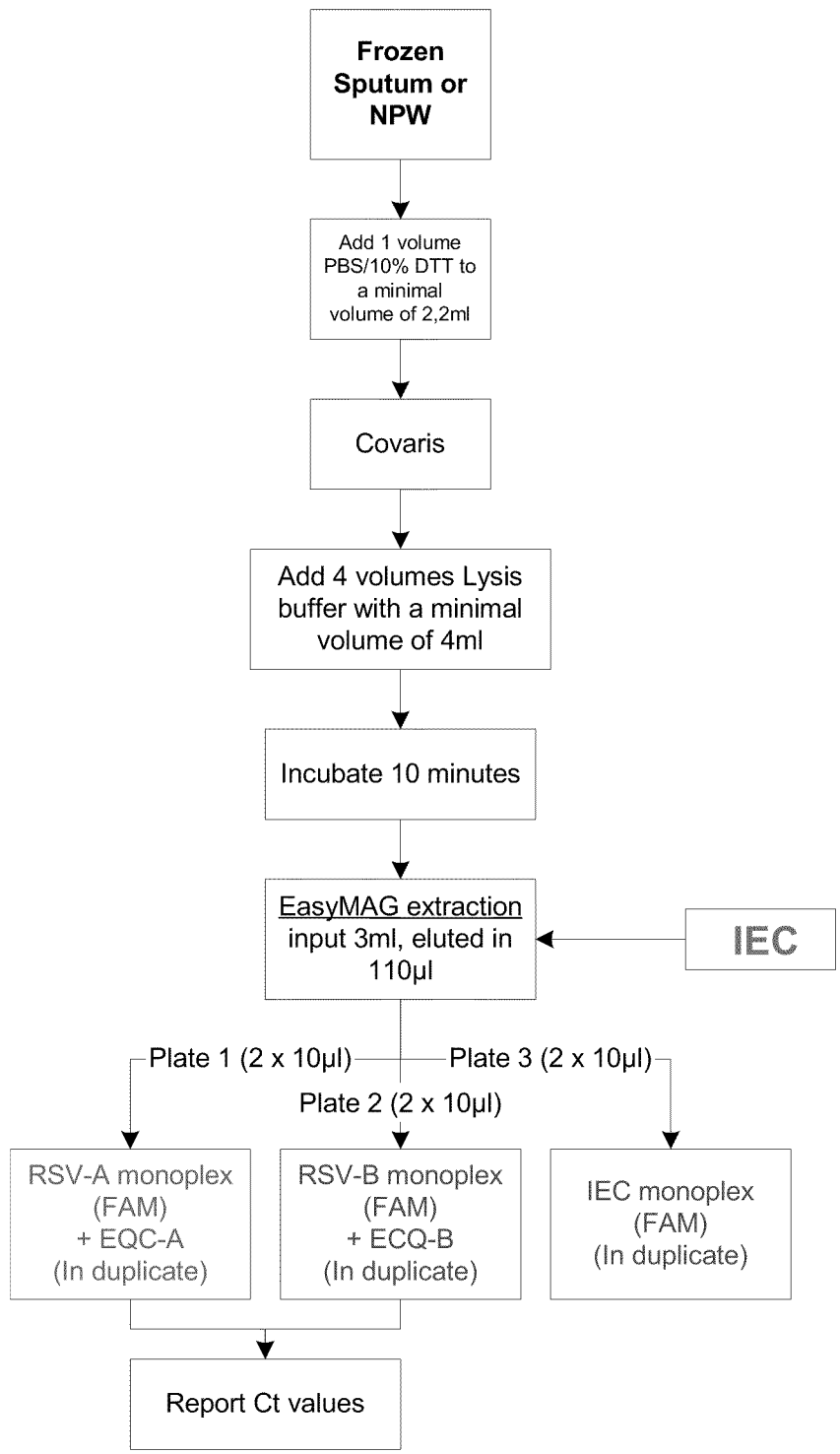

Figure 1. Diagnostic workflow for RSV viral load determination.

A.
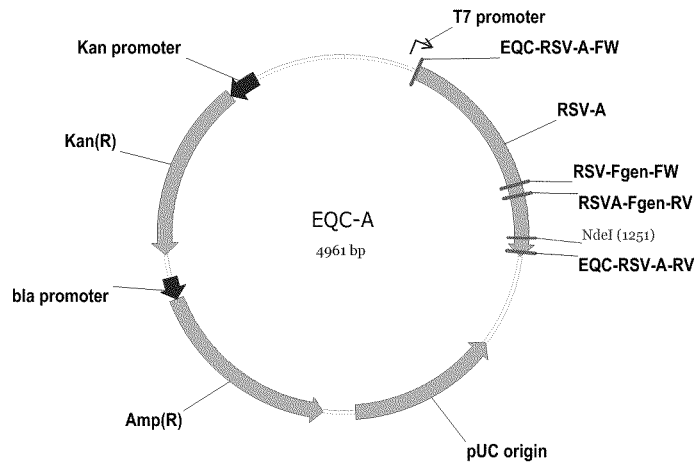
B.
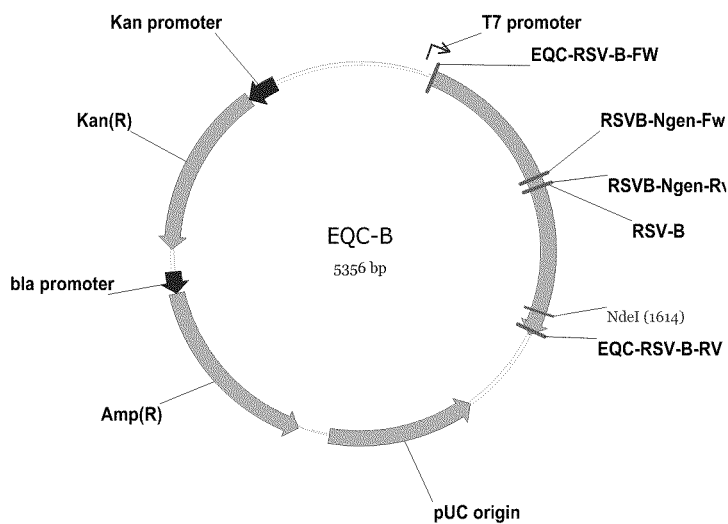
Figure. 4.

(A)
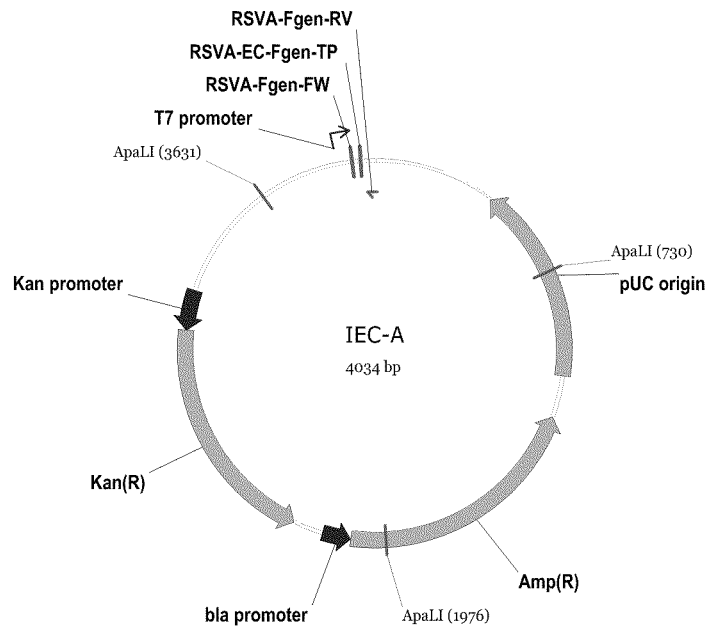
(B)
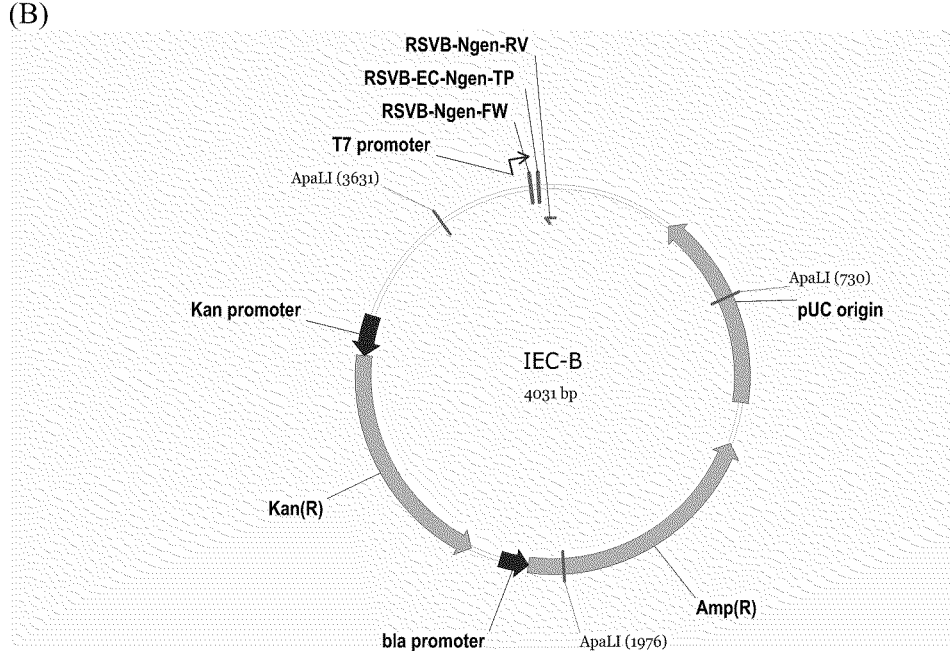
Figure 6

SEQUENCE LISTING

<160> NUMBER OF SEQ ID NOS: 43

<210> SEQ ID NO 1
<211> LENGTH: 27
<212> TYPE: DNA
<213> ORGANISM: Respiratory syncytial virus

<400> SEQUENCE: 1
ctgtgataga rttccaacaa aagaaca                                        27

<210> SEQ ID NO 2
<211> LENGTH: 28
<212> TYPE: DNA
<213> ORGANISM: Respiratory syncytial virus

<400> SEQUENCE: 2
agttacacct gcattaacac taaattcc                                       28

<210> SEQ ID NO 3
<211> LENGTH: 24
<212> TYPE: DNA
<213> ORGANISM: Respiratory syncytial virus -continued

```
<400> SEQUENCE: 3
ggctccagaa tataggcatg attc                                          24

<210> SEQ ID NO 4
<211> LENGTH: 29
<212> TYPE: DNA
<213> ORGANISM: Respiratory syncytial virus

<400> SEQUENCE: 4
tggttattac aagagcagct atacacagt                                     29

<210> SEQ ID NO 5
<211> LENGTH: 19
<212> TYPE: DNA
<213> ORGANISM: Respiratory syncytial virus

<400> SEQUENCE: 5
cagactacta gagattacc                                                19

<210> SEQ ID NO 6
<211> LENGTH: 17
<212> TYPE: DNA
<213> ORGANISM: Respiratory syncytial virus

<400> SEQUENCE: 6
tatcatccca cagtctg                                                  17

<210> SEQ ID NO 7
<211> LENGTH: 19
<212> TYPE: DNA
<213> ORGANISM: Respiratory syncytial virus

<400> SEQUENCE: 7
aatgaccaat ccatacgca                                                19

<210> SEQ ID NO 8
<211> LENGTH: 17
<212> TYPE: DNA
<213> ORGANISM: Respiratory syncytial virus

<400> SEQUENCE: 8
taccgtactc tagccta                                                  17

<210> SEQ ID NO 9
<211> LENGTH: 21
<212> TYPE: DNA
<213> ORGANISM: Respiratory syncytial virus

<400> SEQUENCE: 9
aatcaaaata aactctgggg c                                             21

<210> SEQ ID NO 10
<211> LENGTH: 20
<212> TYPE: DNA
<213> ORGANISM: Respiratory syncytial virus

<400> SEQUENCE: 10
gttggttgta catagagggg                                               20

<210> SEQ ID NO 11
<211> LENGTH: 20
<212> TYPE: DNA
<213> ORGANISM: Respiratory syncytial virus
```

```
<400> SEQUENCE: 11
tacatgtttc agcttgtggg                                            20

<210> SEQ ID NO 12
<211> LENGTH: 21
<212> TYPE: DNA
<213> ORGANISM: Respiratory syncytial virus

<400> SEQUENCE: 12
atatttatca atcatggcgg g                                          21

<210> SEQ ID NO 13
<211> LENGTH: 20
<212> TYPE: DNA
<213> ORGANISM: Respiratory syncytial virus

<400> SEQUENCE: 13
ctacatcatc ttctttgggg                                            20

<210> SEQ ID NO 14
<211> LENGTH: 19
<212> TYPE: DNA
<213> ORGANISM: Respiratory syncytial virus

<400> SEQUENCE: 14
gtgccagatg ttatcgggc                                             19

<210> SEQ ID NO 15
<211> LENGTH: 20
<212> TYPE: DNA
<213> ORGANISM: Respiratory syncytial virus

<400> SEQUENCE: 15
attaaccctc actaaaggga                                            20

<210> SEQ ID NO 16
<211> LENGTH: 20
<212> TYPE: DNA
<213> ORGANISM: Respiratory syncytial virus

<400> SEQUENCE: 16
taatacgact cactataggg                                            20

<210> SEQ ID NO 17
<211> LENGTH: 4961
<212> TYPE: DNA
<213> ORGANISM: Respiratory syncytial virus

<400> SEQUENCE: 17
tgcactggcc aggggatca ccatccgtcg ccccggcgtg tcaataatat cactctgtac      60
atccacaaac agacgataac ggctctctct tttataggtg taaaccttaa actgccgtac    120
gtataggctg cgcaactgtt gggaagggcg atcggtgcgg gcctcttcgc tattacgcca    180
gctggcgaaa gggggatgtg ctgcaaggcg attaagttgg gtaacgccag gttttccca     240 gtcacgacgt tgtaaaacga cggccagtga attgtaatac gactcactat agggcgaatt    300
gaatttagcg gccgcgaatt cgcccttaat caaataaac tctggggcaa ataacaatgg    360
agttgccaat cctcaaagca aatgcaatta ccacaatcct cgctgcagtc acattttgct    420
ttgcttctag tcaaaacatc actgaagaat tttatcaatc aacatgcagt gcagttagca    480
aaggctatct tagtgctcta agaactggtt ggtatactag tgttataact atagaattaa    540
```

| | |
|---|---|
| gtaatatcaa ggaaaataag tgtaatggaa cagatgctaa ggtaaaattg ataaaccaag | 600 |
| aattagataa atataaaaat gctgtaacag aattgcagtt gctcatgcaa agcacaacag | 660 |
| cagcaaacaa tcgagccaga agagaactac caaggtttat gaattataca ctcaacaata | 720 |
| ccaaaaaaac caatgtaaca ttaagcaaga aaaggaaaag aagatttctt ggtttttgt | 780 |
| taggtgttgg atctgcaatc gccagtggca ttgctgtatc taaggtcctg cacttagaag | 840 |
| gagaagtgaa caagatcaaa agtgctctac tatccacaaa caaggccgta gtcagcttat | 900 |
| caaatggagt tagtgtctta accagcaaag tgttagacct caaaaactat atagataaac | 960 |
| aattgttacc tattgtgaat aagcaaagct gcagaatatc aaatatagaa actgtgatag | 1020 |
| agttccaaca aaagaacaac agactactag agattaccag ggaatttagt gttaatgcag | 1080 |
| gtgtaactac acctgtaagc acttacatgt taactaatag tgaattattg tcattaatca | 1140 |
| atgatatgcc tataacaaat gatcagaaaa agttaatgtc caacaatgtt caaatagtta | 1200 |
| gacagcaaag ttactctatc atgtccataa taaaagagga agtcttagca tatgtagtac | 1260 |
| aattaccact atatggtgtg atagatacac cttgttggaa attacacaca tcccctctat | 1320 |
| gtacaaccaa caagggcgaa ttcgtttaaa cctgcaggac tagtcccttt agtgagggtt | 1380 |
| aattctgagc ttggcgtaat catggtcata gctgtttcct gtgtgaaatt gttatccgct | 1440 |
| cacaattcca cacaacatac gagccggaag cataaagtgt aaagcctggg gtgcctaatg | 1500 |
| agtgagctaa ctcacattaa ttgcgttgcg ctcactgccc gctttccagt cgggaaacct | 1560 |
| gtcgtgccag ctgcattaat gaatcggcca acgcgcgggg agaggcggtt tgcgtattgg | 1620 |
| gcgctcttcc gcttcctcgc tcactgactc gctgcgctcg tcgttcggc tgcggcgagc | 1680 |
| ggtatcagct cactcaaagg cggtaatacg gttatccaca gaatcagggg ataacgcagg | 1740 |
| aaagaacatg tgagcaaaag gccagcaaaa gcccaggaac cgtaaaaagg ccgcgttgct | 1800 |
| ggcgtttttc cataggctcc gcccccctga cgagcatcac aaaaatcgac gctcaagtca | 1860 |
| gaggtggcga aacccgacag gactataaag ataccaggcg tttccccctg gaagctccct | 1920 |
| cgtgcgctct cctgttccga ccctgccgct taccggatac ctgtccgcct ttctcccttc | 1980 |
| gggaagcgtg gcgctttctc atagctcacg ctgtaggtat ctcagttcgg tgtaggtcgt | 2040 |
| tcgctccaag ctgggctgtg tgcacgaacc ccccgttcag cccgaccgct gcgccttatc | 2100 |
| cggtaactat cgtcttgagt ccaacccggt aagacacgac ttatcgccac tggcagcagc | 2160 |
| cactggtaac aggattagca gagcgaggta tgtaggcggt gctacagagt tcttgaagtg | 2220 |
| gtggcctaac tacggctaca ctagaaggac agtatttggt atctgcgctc tgctgaagcc | 2280 |
| agttaccttc ggaaaaagag ttggtagctc ttgatccggc aaacaaacca ccgctggtag | 2340 |
| cggtggtttt tttgtttgca agcagcagat tacgcgcaga aaaaaaggat ctcaagaaga | 2400 |
| tcctttgatc ttttctacgg ggtctgacgc tcagtggaac gaaaactcac gttaagggat | 2460 |
| tttggtcatg agattatcaa aaaggatctt cacctagatc cttttaaatt aaaaatgaag | 2520 |
| ttttaaatca atctaaagta tatatgagta aacttggtct gacagttacc aatgcttaat | 2580 |
| cagtgaggca cctatctcag cgatctgtct atttcgttca tccatagttg cctgactccc | 2640 |
| cgtcgtgtag ataactacga tacgggaggg cttaccatct ggccccagtg ctgcaatgat | 2700 |
| accgcgagac ccacgctcac cggctccaga tttatcagca ataaaccagc cagcggaag | 2760 |
| ggccgagcgc agaagtggtc ctgcaacttt atccgcctcc atccagtcta ttaattgttg | 2820 |
| ccgggaagct agagtaagta gttcgccagt taatagtttg cgcaacgttg ttgccattgc | 2880 |
| tacaggcatc gtggtgtcac gctcgtcgtt tggtatggct tcattcagct ccggttccca | 2940 |

```
acgatcaagg cgagttacat gatcccccat gttgtgcaaa aaagcggtta gctccttcgg    3000
tcctccgatc gttgtcagaa gtaagttggc cgcagtgtta tcactcatgg ttatggcagc    3060
actgcataat tctcttactg tcatgccatc cgtaagatgc ttttctgtga ctggtgagta    3120
ctcaaccaag tcattctgag aatagtgtat gcggcgaccg agttgctctt gcccggcgtc    3180
aatacgggat aataccgcgc cacatagcag aactttaaaa gtgctcatca ttggaaaacg    3240
ttcttcgggg cgaaaactct caaggatctt accgctgttg agatccagtt cgatgtaacc    3300
cactcgtgca cccaactgat cttcagcatc ttttactttc accagcgttt ctgggtgagc    3360
aaaaacagga aggcaaaatg ccgcaaaaaa gggaataagg gcgacacgga aatgttgaat    3420
actcatactc ttccttttc aatattattg aagcatttat cagggttatt gtctcatgag    3480
cggatacata tttgaatgta tttagaaaaa taaacaaata ggggttccgc gcacatttcc    3540
ccgaaaagtg ccacctgtat gcggtgtgaa ataccgcaca gatgcgtaag gagaaaatac    3600
cgcatcagga aattgtaagc gttaataatt cagaagaact cgtcaagaag gcgatagaag    3660
gcgatgcgct gcgaatcggg agcggcgata ccgtaaagca cgaggaagcg gtcagcccat    3720
tcgccgccaa gctcttcagc aatatcacgg gtagccaacg ctatgtcctg atagcggtcc    3780
gccacaccca gccggccaca gtcgatgaat ccagaaaagc ggccattttc caccatgata    3840
ttcggcaagc aggcatcgcc atgggtcacg acgagatcct cgccgtcggg catgctcgcc    3900
ttgagcctgg cgaacagttc ggctggcgcg agccctgat gctcttcgtc cagatcatcc    3960
tgatcgacaa gaccggcttc catccgagta cgtgctcgct cgatgcgatg tttcgcttgg    4020
tggtcgaatg ggcaggtagc cggatcaagc gtatgcagcc gccgcattgc atcagccatg    4080
atggatactt tctcggcagg agcaaggtga gatgacagga gatcctgccc cggcacttcg    4140
cccaatagca gccagtccct tcccgcttca gtgacaacgt cgagcacagc tgcgcaagga    4200
acgcccgtcg tggccagcca cgatagccgc gctgcctcgt cttgcagttc attcagggca    4260
ccggacaggt cggtcttgac aaaaagaacc gggcgcccct gcgctgacag ccggaacacg    4320
gcggcatcag agcagccgat tgtctgttgt gcccagtcat agccgaatag cctctccacc    4380
caagcggccg gagaacctgc gtgcaatcca tcttgttcaa tcatgcgaaa cgatcctcat    4440
cctgtctctt gatcagagct tgatccctg cgccatcaga tccttggcgg cgagaaagcc    4500
atccagttta ctttgcaggg cttcccaacc ttaccagagg gcgccccagc tggcaattcc    4560
ggttcgcttg ctgtccataa aaccgcccag tctagctatc gccatgtaag cccactgcaa    4620
gctacctgct ttctctttgc gcttgcgttt tcccttgtcc agatagccca gtagctgaca    4680
ttcatccggg gtcagcaccg tttctgcgga ctggctttct acgtgaaaag gatctaggtg    4740
aagatccttt ttgataatct catgcctgac atttatattc cccagaacat caggttaatg    4800 gcgttttga tgtcattttc gcggtggctg agatcagcca cttcttcccc gataacggag    4860
accggcacac tggccatatc ggtggtcatc atgcgccagc tttcatcccc gatatgcacc    4920
accgggtaaa gttcacggga actttatct gacagcagac g                         4961

<210> SEQ ID NO 18
<211> LENGTH: 5356
<212> TYPE: DNA
<213> ORGANISM: Respiratory syncytial virus

<400> SEQUENCE: 18
tgcactggcc aggggggatca ccatccgtcg ccccggcgtg tcaataatat cactctgtac      60
atccacaaac agacgataac ggctctctct tttataggtg taaaccttaa actgccgtac     120
```

```
gtataggctg cgcaactgtt gggaagggcg atcggtgcgg gcctcttcgc tattacgcca    180
gctggcgaaa gggggatgtg ctgcaaggcg attaagttgg gtaacgccag gttttccca    240
gtcacgacgt tgtaaaacga cggccagtga attgtaatac gactcactat agggcgaatt    300
gaatttagcg gccgcgaatt cgcccttata tttatcaatc atggcgggtt tctagaatgt    360
attggcatta agcctacaaa acacactcct ataatataca aatatgacct caacccgtaa    420
attccaacaa aaaactaacc catccaaact aagctattcc ttaaataaca gtgctcaaca    480
gttaagaagg ggctaatcca ttttagtaat taaaaataaa ggtaaagcca ataacataaa    540
ttggggcaaa tacaaagatg gctcttagca aagtcaagtt aaatgataca ttaaataagg    600
atcagctgct gtcatctagc aaatacacta ttcaacgtag tacaggagat aatattgaca    660
ctcccaatta tgatgtgcaa aaacacttaa acaaactatg tggtatgcta ttaatcactg    720
aagatgcaaa tcataaattc acaggattaa taggtatgtt atatgctatg tccaggttag    780
gaagggaaga cactataaag atacttaaag atgctggata tcatgttaaa gctaatggag    840
tagatataac aacatatcgt caagatataa atggaaagga aatgaaattc gaagtattaa    900
cattatcaag cttgacatca gaaatacaag tcaatattga gatagaatct agaaagtcct    960
acaaaaaaat gctaaaagag atgggagaag tggctccaga atataggcat gattctccag   1020
actgtgggat gataatactg tgtatagctg cacttgtaat aaccaaatta gcagcaggag   1080
atagatcagg tcttacagca gtaattagga gggcaaacaa tgtcttaaaa aacgaaataa   1140
aacgctacaa gggcctcata ccaaggata tagctaacag tttttatgaa gtgtttgaaa   1200
aacaccctca tctttatagat gttttttgtgc actttggcat tgcacaatca tccacaagag   1260
ggggtagtag agttgaagga atcttttgcag gattatttat gaatgcctat ggttcagggc   1320
aagtaatgct aagatgggga gttttagcca aatctgtaaa aaatatcatg ctaggacatg   1380
ctagtgtcca ggcagaaatg gagcaagttg tggaagtcta tgagtatgca cagaagttgg   1440
gaggagaagc tggattctac catatattga acaatccaaa agcatcattg ctgtcattaa   1500
ctcaatttcc taacttctca agtgtggtcc taggcaatgc agcaggtcta ggcataatgg   1560
gagagtatag aggtacacca agaaaccagg atctttatga tgcagccaaa gcatatgcag   1620
agcaactcaa agaaatgga gtaataaact acagtgtatt agacttaaca gcagaagaat   1680
tggaggccat aaaagcatca ctcaacccca agaagatga tgtagaaagg gcgaattcgt   1740
ttaaacctgc aggactagtc cctttagtga gggttaattc tgagcttggc gtaatcatgg   1800
tcatagctgt ttcctgtgtg aaattgttat ccgctcacaa ttccacacaa catacgagcc   1860
ggaagcataa agtgtaaagc ctggggtgcc taatgagtga gctaactcac attaattgcg   1920
ttgcgctcac tgcccgcttt ccagtcggga acctgtcgt gccagctgca ttaatgaatc   1980
ggccaacgcg cggggagagg cggtttgcgt attgggcgct cttccgcttc ctcgctcact   2040
gactcgctgc gctcggtcgt tcggctgcgg cgagcggtat cagctcactc aaaggcggta   2100
atacggttat ccacagaatc aggggataac gcaggaaaga acatgtgagc aaaaggccag   2160
caaaagccca ggaaccgtaa aaaggccgcg ttgctggcgt ttttccatag gctccgcccc   2220
cctgacgagc atcacaaaaa tcgacgctca agtcagaggt ggcgaaaccc gacaggacta   2280
taaagatacc aggcgtttcc ccctggaagc tccctcgtgc gctctcctgt tccgaccctg   2340
ccgcttaccg gatacctgtc cgcctttctc ccttcgggaa gcgtggcgct ttctcatagc   2400
tcacgctgta ggtatctcag ttcggtgtag gtcgttcgct ccaagctggg ctgtgtgcac   2460
gaaccccccg ttcagcccga ccgctgcgcc ttatccggta actatcgtct tgagtccaac   2520
```

```
ccggtaagac acgacttatc gccactggca gcagccactg gtaacaggat tagcagagcg    2580
aggtatgtag gcggtgctac agagttcttg aagtggtggc ctaactacgg ctacactaga    2640
aggacagtat ttggtatctg cgctctgctg aagccagtta ccttcggaaa aagagttggt    2700
agctcttgat ccggcaaaca aaccaccgct ggtagcggtg ttttttttgt ttgcaagcag    2760
cagattacgc gcagaaaaaa aggatctcaa gaagatcctt tgatcttttc tacggggtct    2820
gacgctcagt ggaacgaaaa ctcacgttaa gggattttgg tcatgagatt atcaaaaagg    2880
atcttcacct agatcctttt aaattaaaaa tgaagtttta aatcaatcta agtatatat    2940 gagtaaactt ggtctgacag ttaccaatgc ttaatcagtg aggcacctat ctcagcgatc    3000
tgtctatttc gttcatccat agttgcctga ctccccgtcg tgtagataac tacgatacgg    3060
gagggcttac catctggccc cagtgctgca atgataccgc gagacccacg ctcaccggct    3120
ccagatttat cagcaataaa ccagccagcc ggaagggccg agcgcagaag tggtcctgca    3180
actttatccg cctccatcca gtctattaat tgttgccggg aagctagagt aagtagttcg    3240
ccagttaata gtttgcgcaa cgttgttgcc attgctacag gcatcgtggt gtcacgctcg    3300
tcgtttggta tggcttcatt cagctccggt tcccaacgat caaggcgagt tacatgatcc    3360
cccatgttgt gcaaaaaagc ggttagctcc ttcggtcctc cgatcgttgt cagaagtaag    3420
ttggccgcag tgttatcact catggttatg gcagcactgc ataattctct tactgtcatg    3480
ccatccgtaa gatgcttttc tgtgactggt gagtactcaa ccaagtcatt ctgagaatag    3540
tgtatgcggc gaccgagttg ctcttgcccg gcgtcaatac gggataatac cgcgccacat    3600
agcagaactt taaaagtgct catcattgga aaacgttctt cggggcgaaa actctcaagg    3660
atcttaccgc tgttgagatc cagttcgatg taacccactc gtgcacccaa ctgatcttca    3720
gcatctttta ctttcaccag cgtttctggg tgagcaaaaa caggaaggca aaatgccgca    3780
aaaaagggaa taagggcgac acggaaatgt tgaatactca tactcttcct ttttcaatat    3840
tattgaagca tttatcaggg ttattgtctc atgagcggat acatatttga atgtatttag    3900
aaaaataaac aaataggggt tccgcgcaca tttccccgaa aagtgccacc tgtatgcggt    3960
gtgaaatacc gcacagatgc gtaaggagaa aataccgcat caggaaattg taagcgttaa    4020
taattcagaa gaactcgtca agaaggcgat agaaggcgat gcgctgcgaa tcgggagcgg    4080
cgataccgta aagcacgagg aagcggtcag cccattcgcc gccaagctct tcagcaatat    4140
cacgggtagc caacgctatg tcctgatagc ggtccgccac acccagccgg ccacagtcga    4200
tgaatccaga aaagcggcca ttttccacca tgatattcgg caagcaggca tcgccatggg    4260
tcacgacgag atcctcgccg tcgggcatgc tcgccttgag cctggcgaac agttcggctg    4320
gcgcgagccc ctgatgctct tcgtccagat catcctgatc gacaagaccg gcttccatcc    4380
gagtacgtgc tcgctcgatg cgatgtttcg cttggtggtc gaatgggcag gtagccggat    4440
caagcgtatg cagccgccgc attgcatcag ccatgatgga tactttctcg gcaggagcaa    4500
ggtgagatga caggagatcc tgccccggca cttcgcccaa tagcagccag tcccttcccg    4560
cttcagtgac aacgtcgagc acagctgcgc aaggaacgcc cgtcgtggcc agccacgata    4620
gccgcgctgc ctcgtcttgc agttcattca gggcaccgga caggtcggtc ttgacaaaaa    4680
gaaccgggcg cccctgcgct gacagccgga acacggcggc atcagagcag ccgattgtct    4740
gttgtgccca gtcatagccg aatagcctct ccacccaagc ggccggagaa cctgcgtgca    4800
atccatcttg ttcaatcatg cgaaacgatc ctcatcctgt ctcttgatca gagcttgatc    4860
ccctgcgcca tcagatcctt ggcggcgaga aagccatcca gtttactttg cagggcttcc    4920
```

| | |
|---|---|
| caaccttacc agagggcgcc ccagctggca attccggttc gcttgctgtc cataaaaccg | 4980 |
| cccagtctag ctatcgccat gtaagcccac tgcaagctac ctgctttctc tttgcgcttg | 5040 |
| cgttttccct tgtccagata gcccagtagc tgacattcat ccggggtcag caccgtttct | 5100 |
| gcggactggc tttctacgtg aaaaggatct aggtgaagat cctttttgat aatctcatgc | 5160 |
| ctgacattta tattccccag aacatcaggt taatggcgtt tttgatgtca ttttcgcggt | 5220 |
| ggctgagatc agccacttct tccccgataa cggagaccgg cacactggcc atatcggtgg | 5280 |
| tcatcatgcg ccagctttca tccccgatat gcaccaccgg gtaaagttca cgggagactt | 5340 |
| tatctgacag cagacg | 5356 |

<210> SEQ ID NO 19
<211> LENGTH: 43
<212> TYPE: DNA
<213> ORGANISM: Respiratory syncytial virus

<400> SEQUENCE: 19

| | |
|---|---|
| ctgtgataga gttccaacaa aagaacaatg cgtatggatt ggt | 43 |

<210> SEQ ID NO 20
<211> LENGTH: 43
<212> TYPE: DNA
<213> ORGANISM: Respiratory syncytial virus

<400> SEQUENCE: 20

| | |
|---|---|
| agttacacct gcattaacac taaattccct aatgaccaat cca | 43 |

<210> SEQ ID NO 21
<211> LENGTH: 41
<212> TYPE: DNA
<213> ORGANISM: Respiratory syncytial virus

<400> SEQUENCE: 21

| | |
|---|---|
| ggctccagaa tataggcatg attctctacc gtactctagc c | 41 |

<210> SEQ ID NO 22
<211> LENGTH: 41
<212> TYPE: DNA
<213> ORGANISM: Respiratory syncytial virus

<400> SEQUENCE: 22

| | |
|---|---|
| tggttattac aagtgctgct atacacagta ttaggctaga g | 41 |

<210> SEQ ID NO 23
<211> LENGTH: 4034
<212> TYPE: DNA
<213> ORGANISM: Respiratory syncytial virus

<400> SEQUENCE: 23

| | |
|---|---|
| tgcactggcc aggggatca ccatccgtcg ccccggcgtg tcaataatat cactctgtac | 60 |
| atccacaaac agacgataac ggctctctct tttataggtg taaaccttaa actgccgtac | 120 |
| gtataggctg cgcaactgtt gggaagggcg atcggtgcgg gcctcttcgc tattacgcca | 180 |
| gctggcgaaa gggggatgtg ctgcaaggcg attaagttgg gtaacgccag ggttttccca | 240 |
| gtcacgacgt tgtaaaacga cggccagtga attgtaatac gactcactat agggcgaatt | 300 |
| gaatttagcg gccgcgaatt cgcccttctg tgatagagtt ccaacaaaag aacaatgcgt | 360 |
| atggattggt cattagggaa tttagtgtta atgcaggtgt aactaagggc gaattcgttt | 420 |
| aaacctgcag gactagtccc tttagtgagg gttaattctg agcttggcgt aatcatggtc | 480 |

```
atagctgttt cctgtgtgaa attgttatcc gctcacaatt ccacacaaca tacgagccgg    540
aagcataaag tgtaaagcct ggggtgccta atgagtgagc taactcacat taattgcgtt    600
gcgctcactg cccgctttcc agtcgggaaa cctgtcgtgc cagctgcatt aatgaatcgg    660
ccaacgcgcg gggagaggcg gtttgcgtat tgggcgctct tccgcttcct cgctcactga    720
ctcgctgcgc tcggtcgttc ggctgcggcg agcggtatca gctcactcaa aggcggtaat    780
acggttatcc acagaatcag gggataacgc aggaaagaac atgtgagcaa aaggccagca    840
aaagcccagg aaccgtaaaa aggccgcgtt gctggcgttt ttccataggc tccgcccccc    900
tgacgagcat cacaaaaatc gacgctcaag tcagaggtgg cgaaacccga caggactata    960
aagataccag gcgtttcccc ctggaagctc cctcgtgcgc tctcctgttc cgaccctgcc   1020
gcttaccgga tacctgtccg cctttctccc ttcgggaagc gtggcgcttt ctcatagctc   1080
acgctgtagg tatctcagtt cggtgtaggt cgttcgctcc aagctgggct gtgtgcacga   1140
accccccgtt cagcccgacc gctgcgcctt atccggtaac tatcgtcttg agtccaaccc   1200
ggtaagacac gacttatcgc cactggcagc agccactggt aacaggatta gcagagcgag   1260
gtatgtaggc ggtgctacag agttcttgaa gtggtggcct aactacggct acactagaag   1320
gacagtattt ggtatctgcg ctctgctgaa gccagttacc ttcggaaaaa gagttggtag   1380
ctcttgatcc ggcaaacaaa ccaccgctgg tagcggtggt ttttttgttt gcaagcagca   1440
gattacgcgc agaaaaaaag gatctcaaga agatcctttg atcttttcta cggggtctga   1500
cgctcagtgg aacgaaaact cacgttaagg gattttggtc atgagattat caaaaaggat   1560
cttcacctag atccttttaa attaaaaatg aagttttaaa tcaatctaaa gtatatatga   1620
gtaaacttgg tctgacagtt accaatgctt aatcagtgag gcacctatct cagcgatctg   1680
tctatttcgt tcatccatag ttgcctgact ccccgtcgtg tagataacta cgatacggga   1740
gggcttacca tctggcccca gtgctgcaat gataccgcga gacccacgct caccggctcc   1800
agatttatca gcaataaacc agccagccgg aagggccgag cgcagaagtg gtcctgcaac   1860
tttatccgcc tccatccagt ctattaattg ttgccgggaa gctagagtaa gtagttcgcc   1920
agttaatagt ttgcgcaacg ttgttgccat tgctacaggc atcgtggtgt cacgctcgtc   1980
gtttggtatg gcttcattca gctccggttc ccaacgatca aggcgagtta catgatcccc   2040
catgttgtgc aaaaaagcgg ttagctcctt cggtcctccg atcgttgtca gaagtaagtt   2100
ggccgcagtg ttatcactca tggttatggc agcactgcat aattctctta ctgtcatgcc   2160
atccgtaaga tgcttttctg tgactggtga gtactcaacc aagtcattct gagaatagtg   2220
tatgcggcga ccgagttgct cttgcccggc gtcaatacgg gataataccg cgccacatag   2280
cagaacttta aaagtgctca tcattggaaa acgttcttcg gggcgaaaac tctcaaggat   2340
cttaccgctg ttgagatcca gttcgatgta acccactcgt gcacccaact gatcttcagc   2400
atcttttact ttcaccagcg tttctgggtg agcaaaaaca ggaaggcaaa atgccgcaaa   2460
aaagggaata agggcgacac ggaaatgttg aatactcata ctcttccttt ttcaatatta   2520
ttgaagcatt tatcagggtt attgtctcat gagcggatac atatttgaat gtatttagaa   2580
aaataaacaa ataggggttc cgcgcacatt tccccgaaaa gtgccacctg tatgcggtgt   2640
gaaataccgc acagatgcgt aaggagaaaa taccgcatca ggaaattgta agcgttaata   2700
attcagaaga actcgtcaag aaggcgatag aaggcgatgc gctgcgaatc gggagcggcg   2760
ataccgtaaa gcacgaggaa gcggtcagcc cattcgccgc caagctcttc agcaatatca   2820
cgggtagcca acgctatgtc ctgatagcgg tccgccacac ccagccggcc acagtcgatg   2880
```

| | |
|---|---:|
| aatccagaaa agcggccatt ttccaccatg atattcggca agcaggcatc gccatgggtc | 2940 |
| acgacgagat cctcgccgtc gggcatgctc gccttgagcc tggcgaacag ttcggctggc | 3000 |
| gcgagcccct gatgctcttc gtccagatca tcctgatcga caagaccggc ttccatccga | 3060 |
| gtacgtgctc gctcgatgcg atgtttcgct tggtggtcga atgggcaggt agccggatca | 3120 |
| agcgtatgca gccgccgcat tgcatcagcc atgatggata cttttctcggc aggagcaagg | 3180 |
| tgagatgaca ggagatcctg ccccggcact tcgcccaata gcagccagtc ccttcccgct | 3240 |
| tcagtgacaa cgtcgagcac agctgcgcaa ggaacgcccg tcgtggccag ccacgatagc | 3300 |
| cgcgctgcct cgtcttgcag ttcattcagg gcaccggaca ggtcggtctt gacaaaaaga | 3360 |
| accgggcgcc cctgcgctga cagccggaac acggcggcat cagagcagcc gattgtctgt | 3420 |
| tgtgcccagt catagccgaa tagcctctcc acccaagcgg ccggagaacc tgcgtgcaat | 3480 |
| ccatcttgtt caatcatgcg aaacgatcct catcctgtct cttgatcaga gcttgatccc | 3540 |
| ctgcgccatc agatccttgg cggcgagaaa gccatccagt ttactttgca gggcttccca | 3600 |
| accttaccag agggcgcccc agctggcaat tccggttcgc ttgctgtcca taaaaccgcc | 3660 |
| cagtctagct atcgccatgt aagcccactg caagctacct gctttctctt tgcgcttgcg | 3720 |
| ttttcccttg tccagatagc ccagtagctg acattcatcc ggggtcagca ccgtttctgc | 3780 |
| ggactggctt tctacgtgaa aaggatctag gtgaagatcc tttttgataa tctcatgcct | 3840 |
| gacatttata ttccccagaa catcaggtta atggcgtttt tgatgtcatt ttcgcggtgg | 3900 |
| ctgagatcag ccacttcttc cccgataacg gagaccggca cactggccat atcggtggtc | 3960 |
| atcatgcgcc agctttcatc cccgatatgc accaccgggt aaagttcacg ggagacttta | 4020 |
| tctgacagca gacg | 4034 |

<210> SEQ ID NO 24
<211> LENGTH: 4031
<212> TYPE: DNA
<213> ORGANISM: Respiratory syncytial virus

<400> SEQUENCE: 24

| | |
|---|---:|
| tgcactggcc aggggatca ccatccgtcg ccccggcgtg tcaataatat cactctgtac | 60 |
| atccacaaac agacgataac ggctctctct tttataggtg taaaccttaa actgccgtac | 120 |
| gtataggctg cgcaactgtt gggaagggcg atcggtgcgg gcctcttcgc tattacgcca | 180 |
| gctggcgaaa gggggatgtg ctgcaaggcg attaagttgg gtaacgccag ggttttccca | 240 |
| gtcacgacgt tgtaaaacga cggccagtga attgtaatac gactcactat agggcgaatt | 300 |
| gaatttagcg gccgcgaatt cgcccttggc tccagaatat aggcatgatt ctctaccgta | 360 |
| ctctagccta atactgtgta tagcagcact tgtaataacc aaagggcgaa ttcgtttaaa | 420 |
| cctgcaggac tagtcccttt agtgagggtt aattctgagc ttggcgtaat catggtcata | 480 |
| gctgtttcct gtgtgaaatt gttatccgct cacaattcca cacaacatac gagccggaag | 540 |
| cataaagtgt aaagcctggg gtgcctaatg agtgagctaa ctcacattaa ttgcgttgcg | 600 |
| ctcactgccc gctttccagt cgggaaacct gtcgtgccag ctgcattaat gaatcggcca | 660 |
| acgcgcgggg agaggcggtt tgcgtattgg gcgctcttcc gcttcctcgc tcactgactc | 720 |
| gctgcgctcg tcgttcggc tgcggcgagc ggtatcagct cactcaaagg cggtaatacg | 780 |
| gttatccaca gaatcagggg ataacgcagg aaagaacatg tgagcaaaag gccagcaaaa | 840 |
| gcccaggaac cgtaaaaagg ccgcgttgct ggcgtttttc cataggctcc gcccccctga | 900 |
| cgagcatcac aaaaatcgac gctcaagtca gaggtggcga aacccgacag gactataaag | 960 |

```
ataccaggcg tttccccctg gaagctccct cgtgcgctct cctgttccga ccctgccgct   1020
taccggatac ctgtccgcct ttctcccttc gggaagcgtg gcgctttctc atagctcacg   1080
ctgtaggtat ctcagttcgg tgtaggtcgt tcgctccaag ctgggctgtg tgcacgaacc   1140
ccccgttcag cccgaccgct gcgccttatc cggtaactat cgtcttgagt ccaacccggt   1200
aagacacgac ttatcgccac tggcagcagc cactggtaac aggattagca gagcgaggta   1260
tgtaggcggt gctacagagt tcttgaagtg gtggcctaac tacggctaca ctagaaggac   1320
agtatttggt atctgcgctc tgctgaagcc agttaccttc ggaaaaagag ttggtagctc   1380
ttgatccggc aaacaaacca ccgctggtag cggtggtttt tttgtttgca agcagcagat   1440
tacgcgcaga aaaaaggat ctcaagaaga tcctttgatc ttttctacgg gtctgacgc    1500
tcagtggaac gaaaactcac gttaagggat tttggtcatg agattatcaa aaggatctt    1560
cacctagatc cttttaaatt aaaaatgaag ttttaaatca atctaaagta tatatgagta   1620
aacttggtct gacagttacc aatgcttaat cagtgaggca cctatctcag cgatctgtct   1680
atttcgttca tccatagttg cctgactccc cgtcgtgtag ataactacga tacgggaggg   1740
cttaccatct ggccccagtg ctgcaatgat accgcgagac ccacgctcac cggctccaga   1800
tttatcagca ataaaccagc cagccggaag ggccgagcgc agaagtggtc ctgcaacttt   1860
atccgcctcc atccagtcta ttaattgttg ccgggaagct agagtaagta gttcgccagt   1920
taatagtttg cgcaacgttg ttgccattgc tacaggcatc gtggtgtcac gctcgtcgtt   1980
tggtatggct tcattcagct ccggttccca acgatcaagg cgagttacat gatccccat    2040
gttgtgcaaa aaagcggtta gctccttcgg tcctccgatc gttgtcagaa gtaagttggc   2100
cgcagtgtta tcactcatgg ttatggcagc actgcataat tctcttactg tcatgccatc   2160
cgtaagatgc ttttctgtga ctggtgagta ctcaaccaag tcattctgag aatagtgtat   2220
gcggcgaccg agttgctctt gcccggcgtc aatacgggat aataccgcgc cacatagcag   2280
aactttaaaa gtgctcatca ttggaaaacg ttcttcgggg cgaaaactct caaggatctt   2340
accgctgttg agatccagtt cgatgtaacc cactcgtgca cccaactgat cttcagcatc   2400
ttttactttc accagcgttt ctgggtgagc aaaaacagga aggcaaaatg ccgcaaaaaa   2460
gggaataagg gcgacacgga aatgttgaat actcatactc ttccttttc aatattattg    2520
aagcatttat cagggttatt gtctcatgag cggatacata tttgaatgta tttagaaaaa   2580
taaacaaata ggggttccgc gcacatttcc ccgaaaagtg ccacctgtat gcggtgtgaa   2640
ataccgcaca gatgcgtaag gagaaaatac cgcatcagga aattgtaagc gttaataatt   2700
cagaagaact cgtcaagaag gcgatagaag gcgatgcgct gcgaatcggg agcggcgata   2760
ccgtaaagca cgaggaagcg gtcagcccat tcgccgccaa gctcttcagc aatatcacgg   2820
gtagccaacg ctatgtcctg atagcggtcc gccacaccca gccggccaca gtcgatgaat   2880
ccagaaaagc ggccatttc caccatgata ttcggcaagc aggcatcgcc atgggtcacg    2940
acgagatcct cgccgtcggg catgctcgcc ttgagcctgg cgaacagttc ggctggcgcg   3000
agccctgat gctcttcgtc cagatcatcc tgatcgacaa gaccggcttc catccgagta    3060
cgtgctcgct cgatgcgatg tttcgcttgg tggtcgaatg ggcaggtagc cggatcaagc   3120
gtatgcagcc gccgcattgc atcagccatg atggatactt tctcggcagg agcaaggtga   3180
gatgacagga gatcctgccc cggcacttcg cccaatagca gccagtccct tcccgcttca   3240
gtgacaacgt cgagcacagc tgcgcaagga acgcccgtcg tggccagcca cgatagccgc   3300
gctgcctcgt cttgcagttc attcagggca ccggacaggt cggtcttgac aaaaagaacc   3360
```

-continued

| | |
|---|---|
| gggcgcccct gcgctgacag ccggaacacg gcggcatcag agcagccgat tgtctgttgt | 3420 |
| gcccagtcat agccgaatag cctctccacc caagcggccg gagaacctgc gtgcaatcca | 3480 |
| tcttgttcaa tcatgcgaaa cgatcctcat cctgtctctt gatcagagct tgatcccctg | 3540 |
| cgccatcaga tccttggcgg cgagaaagcc atccagttta ctttgcaggg cttcccaacc | 3600 |
| ttaccagagg gcgccccagc tggcaattcc ggttcgcttg ctgtccataa aaccgcccag | 3660 |
| tctagctatc gccatgtaag cccactgcaa gctacctgct ttctctttgc gcttgcgttt | 3720 |
| tcccttgtcc agatagccca gtagctgaca ttcatccggg gtcagcaccg tttctgcgga | 3780 |
| ctggctttct acgtgaaaag gatctaggtg aagatccttt ttgataatct catgcctgac | 3840 |
| atttatattc cccagaacat caggttaatg gcgttttttga tgtcattttc gcggtggctg | 3900 |
| agatcagcca cttcttcccc gataacggag accggcacac tggccatatc ggtggtcatc | 3960 |
| atgcgccagc tttcatcccc gatatgcacc accgggtaaa gttcacggga gactttatct | 4020 |
| gacagcagac g | 4031 |

<210> SEQ ID NO 25
<211> LENGTH: 39
<212> TYPE: DNA
<213> ORGANISM: Respiratory syncytial virus

<400> SEQUENCE: 25
cagactacta gagattacca tacaacgaga ggaaaccctt    39

<210> SEQ ID NO 26
<211> LENGTH: 37
<212> TYPE: DNA
<213> ORGANISM: Respiratory syncytial virus

<400> SEQUENCE: 26
tgcccaggga ggctagcggg aatttagtgt taatgca    37

<210> SEQ ID NO 27
<211> LENGTH: 38
<212> TYPE: DNA
<213> ORGANISM: Respiratory syncytial virus

<400> SEQUENCE: 27
agactgtggg atgataatac tacaacgagg ttgtgctg    38

<210> SEQ ID NO 28
<211> LENGTH: 37
<212> TYPE: DNA
<213> ORGANISM: Respiratory syncytial virus

<400> SEQUENCE: 28
cggttggtga ggctagctgt gtatagctgc acttgta    37

<210> SEQ ID NO 29
<211> LENGTH: 38
<212> TYPE: DNA
<213> ORGANISM: Respiratory syncytial virus

<400> SEQUENCE: 29
acctgcagga ctagtccctt tacaacgaga ggcgtgat    38

<210> SEQ ID NO 30
<211> LENGTH: 37
<212> TYPE: DNA
<213> ORGANISM: Respiratory syncytial virus -continued

```
<400> SEQUENCE: 30
ctgggaggaa ggctagctag tgagggttaa ttctgag                                37

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
aaggtttcct cguccctggg ca                                                22

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
cagcacaacc gucaccaacc g                                                 21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
atcacgcctc gutcctccca g                                                 21

<210> SEQ ID NO 34
<211> LENGTH: 22
<212> TYPE: DNA
<213> ORGANISM: Respiratory syncytial virus

<400> SEQUENCE: 34
gtgatagagt tccaacaaaa ga                                                22

<210> SEQ ID NO 35
<211> LENGTH: 21
<212> TYPE: DNA
<213> ORGANISM: Respiratory syncytial virus

<400> SEQUENCE: 35
aagtgcttac aggtgtagtt a                                                 21

<210> SEQ ID NO 36
<211> LENGTH: 21
<212> TYPE: DNA
<213> ORGANISM: Respiratory syncytial virus

<400> SEQUENCE: 36
```

```
gctccagaat ataggcatga t                                              21

<210> SEQ ID NO 37
<211> LENGTH: 21
<212> TYPE: DNA
<213> ORGANISM: Respiratory syncytial virus

<400> SEQUENCE: 37
gatctatctc ctgctgctaa t                                              21

<210> SEQ ID NO 38
<211> LENGTH: 21
<212> TYPE: DNA
<213> ORGANISM: Respiratory syncytial virus

<400> SEQUENCE: 38
cttgtaataa ccaaagggcg a                                              21

<210> SEQ ID NO 39
<211> LENGTH: 22
<212> TYPE: DNA
<213> ORGANISM: Respiratory syncytial virus

<400> SEQUENCE: 39
ggaaacagct atgaccatga tt                                             22

<210> SEQ ID NO 40
<211> LENGTH: 77
<212> TYPE: DNA
<213> ORGANISM: Respiratory syncytial virus

<400> SEQUENCE: 40
ctgtgataga gttccaacaa aagaacaaca gactactaga gattaccagg gaatttagtg    60
ttaatgcagg tgtaact                                                   77

<210> SEQ ID NO 41
<211> LENGTH: 77
<212> TYPE: DNA
<213> ORGANISM: Respiratory syncytial virus

<400> SEQUENCE: 41
ctgtgataga gttccaacaa aagaacaatg cgtatggatt ggtcattagg gaatttagtg    60
ttaatgcagg tgtaact                                                   77

<210> SEQ ID NO 42
<211> LENGTH: 74
<212> TYPE: DNA
<213> ORGANISM: Respiratory syncytial virus

<400> SEQUENCE: 42
ggctccagaa tataggcatg attctccaga ctgtgggatg ataatactgt gtatagctgc    60
tcttgtaata acca                                                      74

<210> SEQ ID NO 43
<211> LENGTH: 74
<212> TYPE: DNA
<213> ORGANISM: Respiratory syncytial virus
```

-continued

<400> SEQUENCE: 43
ggctccagaa tataggcatg attctctacc gtactctagc ctaatactgt gtatagctgc    60
tcttgtaata acca    74

RESPIRATORY SYNCYTIAL VIRUS (RSV) VIRAL LOAD DETECTION ASSAY

CROSS REFERENCE TO RELATED APPLICATIONS

This application is the national stage of PCT Application No. PCT/EP2008/054073 filed Apr. 4, 2008, which claims priority from European Patent Application No. 07108211.9, filed May 15, 2007, and European Patent Application No. 07105823.4 filed Apr. 6, 2007, the entire disclosures of which are hereby incorporated in their entirety.

NAMES OF THE PARTIES TO A JOINT RESEARCH AGREEMENT

The subject matter of this application was developed under a joint research agreement between Johnson and Johnson Research Pty Limited, Virco BVBA and Tibotec Pharmaceuticals, effective Sep. 13, 2006.

The invention relates to a method for the extraction of nucleic acids from biological samples e.g. tissue material or sputum derived from human or animal species and the quantitative detection thereafter of said nucleic acids e.g. in terms of viral load, more specifically RSV viral load detection.

Human respiratory syncytial virus (RSV) is a negative sense, single-stranded RNA virus of the family Paramyxoviridae, which includes common respiratory viruses such as those causing measles and mumps. RSV is a member of the paramyxovirus subfamily Pneumovirinae. The virion is variable in shape and size (average diameter of between 120 and 300 nm), is unstable in the environment (surviving only a few hours on environmental surfaces), and is readily inactivated with soap and water and disinfectants.

Clinical features: Respiratory syncytial virus (RSV) is the most common cause of bronchiolitis and pneumonia among infants and children under 1 year of age. Illness begins most frequently with fever, runny nose, cough, and sometimes wheezing. During their first RSV infection, between 25% and 40% of infants and young children have signs or symptoms of bronchiolitis or pneumonia, and 0.5% to 2% require hospitalization. Most children recover from illness in 8 to 15 days. The majority of children hospitalized for RSV infection are under 6 months of age. RSV also causes repeated infections throughout life, usually associated with moderate-to-severe cold-like symptoms; however, severe lower respiratory tract disease may occur at any age, especially among the elderly or among those with compromised cardiac, pulmonary, or immune systems.

Epidemiologic features: RSV is spread from respiratory secretions through close contact with infected persons or contact with contaminated surfaces or objects. Infection can occur when infectious material contacts mucous membranes of the eyes, mouth, or nose, and possibly through the inhalation of droplets generated by a sneeze or cough. In temperate climates, RSV infections usually occur during annual community outbreaks, often-lasting 4 to 6 months, during the late fall, winter, or early spring months. The timing and severity of outbreaks in a community vary from year to year. RSV spreads efficiently among children during the annual outbreaks, and most children will have serologic evidence of RSV infection by 2 years of age.

Diagnosis: Diagnosis of RSV infection can be made by virus isolation, detection of viral antigens, detection of viral RNA, demonstration of a rise in serum antibodies, or a combination of these approaches. Clinical laboratories use either antigen detection assays to diagnose infection or nucleic acid amplification techniques to detect viral nucleic acids.

To demonstrate antiviral activity of pharmaceutical compounds on the market or in development, a sensitive viral load test or assay is needed to measure any drop in RSV viral load upon treatment with the compound(s).

Viral load is a measure of the severity of a viral infection, and can be calculated by determining the amount of virus in an involved body fluid, for example, it can be given in nucleic acid copies per milliliter of blood. Determination of viral load is part of the therapy monitoring during chronic viral infections for instance in immunocompromised patients.

Thus, there is an ongoing need in the art for simple, fast and cost effective methods for detecting, identifying and quantifying RSV in biological samples in terms of viral load. Biological samples can be obtained from any organism but are preferably from human or animal origin.

Preferably such a method must be able to process RNA derived from sputum and naso-pharyngeal wash (NPW). As a consequence thereof the detection assay, i.e. the RSV viral load detection assay, must include a sputum and NPW treatment method in preparation for RNA extraction from these samples. The assay must also be quantitative and able to distinguish between RSV-A and RSV-B in order not to miss a potential shift in RSV outbreak in a certain season.

The problem with sputum and NPW is that aliquots thereof are quite difficult to handle especially with regard to the extraction of nucleic acid material from said aliquots. Using the so-called EasyMAG® procedure (BioMérieux) for the extraction of nucleic acid material (such as RNA) from a sample, requires a more or less liquid solution for the extraction of nucleic acid from said solution. It is obvious that sputum, lung tissue but also NPW or cellular fractions containing RSV to be detected, do not qualify as a feasible liquid solution for further nucleic acid extraction thereof.

The solution is now found in a treatment method of samples, especially sputum and NPW, prior to the extraction of nucleic acid from said samples. After the extraction of nucleic acid from the samples, the nucleic acid is quantified e.g. viral load detection either by an additional real-time Polymerase Chain Reaction (q-RT-PCR) or additional by the so-called multi component nucleic acid enzyme technology (MNAzyme).

The inventive method for treating samples, whereafter an extraction method is used for isolation and subsequent detection of nucleic acids (RNA and/or DNA), is not limited to RSV RNA containing samples but can be applied for the detection of any viral (RNA or DNA) or bacterial (DNA) respiratory pathogen such as but not limited to Influenza A and B, Para-influenza types 1, 2, 3 and/or 4, meta-pneumovirus, rhinovirus and adenovirus.

In accordance with the present invention a method for the extraction of nucleic acids from a biological sample has been found comprising the following steps:
 a) obtaining a biological sample (e.g. tissue material from a human being or animal species,
 b) adding phosphate buffered saline/10% dithiothreitol to said tissue material of step a),
 c) incubating under ultrasonic conditions,
 d) adding lysis buffer,
 e) obtaining lysed tissue material and
 f) extracting said nucleic acid from said lysed tissue material.

Above mentioned step c) is preferably performed with a so-called Covaris S2 ultrasonic apparatus while the extraction step f) is preferably performed using the so-called EasyMAG procedure (BioMérieux).

Above mentioned step c) can alternatively be a mixing step using a Dyspomix apparatus specifically for (lung) tissue.

The nucleic acid can be either or both DNA or RNA from pathogens such as viruses or any other micro-organism while said tissue material can be either frozen sputum, naso-pharyngeal wash (NPW) or lung tissue wherein said virus is for instance human respiratory syncytial virus (RSV).

Said nucleic acid is further quantified by either the so-called quantitative real time Polymerase Chain Reaction technology (q-RT PCR) or by the so-called multi component nucleic acid enzyme technology (MNAzyme).

The combination of the above described extraction method of nucleic acid preferably from RSV containing patient samples with the further quantification by either q-RT-PCR or by the MNAzyme technology is also part of the present invention.

The invention further relates to a method for identifying, detecting or quantifying the presence of at least one target Respiratory Syncytial Virus (RSV) comprising the following steps:

(a) providing two or more oligonucleotide components wherein at least a first oligonucleotide component and at least a second oligonucleotide component are capable of self-assembly in the presence of said target to form a catalytically active multi-component nucleic acid enzyme (MNAzyme);

(b) contacting said oligonucleotide components with a sample putatively containing said at least one target under conditions:
  (1) permitting the binding of said target to said oligonucleotide components and
  (2) permitting the catalytic activity of the MNAzyme; and (c) identifying, detecting or quantifying the presence of the catalytic activity of the MNAzyme, wherein the presence of the catalytic activity is indicative of the presence of said target.

Preferably the viral load of the target, RSV, is quantified by the above-mentioned method.

For a detailed explanation of q-RT-PCR technology specific reference is made to EP 543, 942 filed by F. Hoffmann-La Roche AG, Switzerland, while the MNAzyme technology is explained in great detail in patent application PCT/AU2006/001473 filed by Johnson & Johnson Research Pty Limited, Australia) and both documents are herewith incorporated by reference for sake of detailed explanation of both technologies.

Regarding the MNAzyme technology a general description of said technology is given hereafter.

Figure 2:
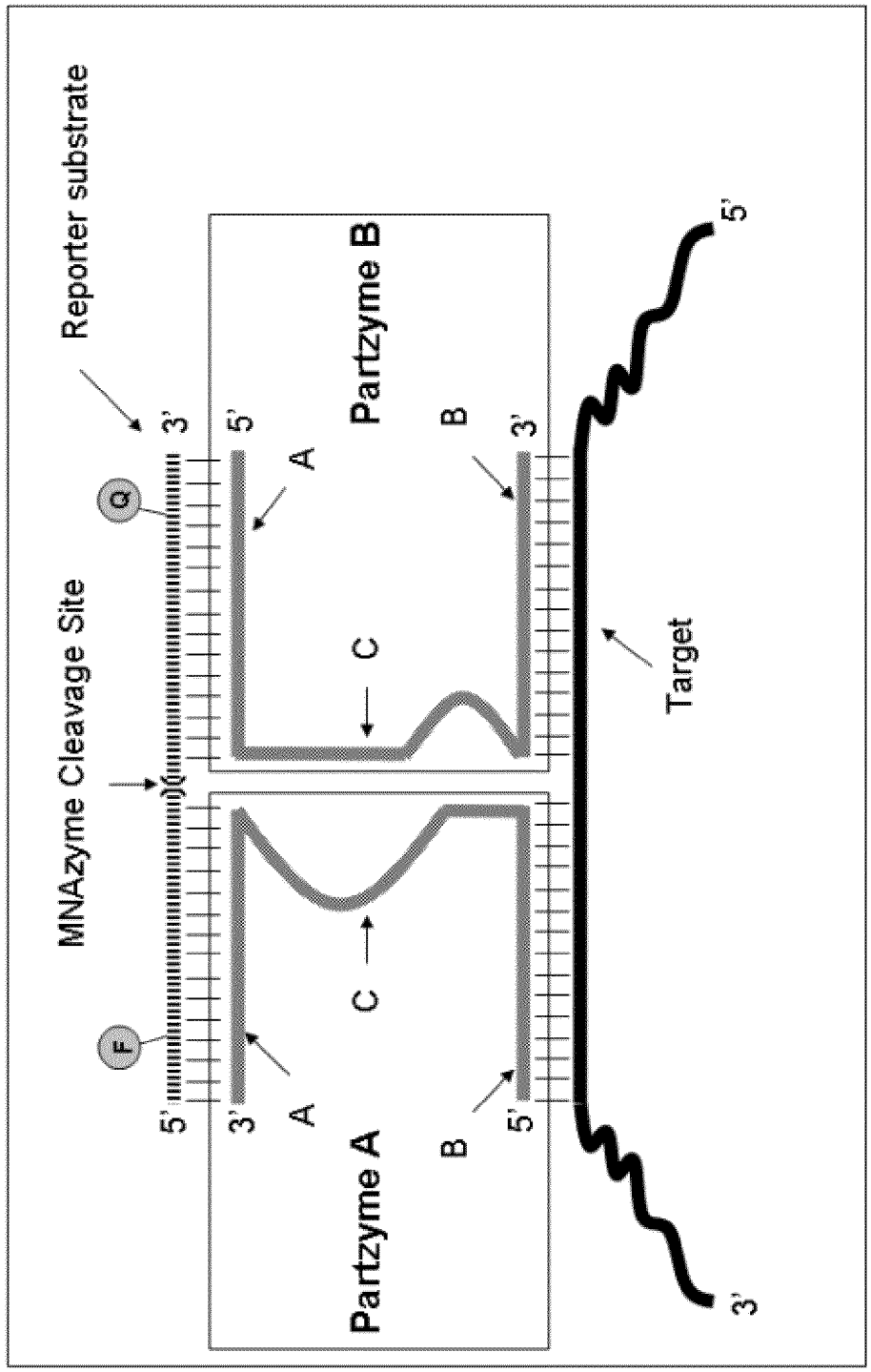

MNAzymes (patent application PCT/AU2006/001473 by Johnson & Johnson Research Pty Limited, Australia) are novel catalytic nucleic acids based on DNAzymes. MNAzymes consist of two or more oligonucleotide sequences (e.g. partzymes) which, only in the presence of a MNAzyme assembly facilitator molecule (e.g. target which may be quantitatively amplified), form an active nucleic acid enzyme that is capable of catalytically modifying a substrate, for example a reporter substrate. An exemplary MNAzyme comprising partzyme A and partzyme B is depicted in FIG. 2. With reference to FIG. 2, DNA partzymes A and B each bind to a target, i.e. the MNAzyme assembly facilitator molecule (e.g., through Watson-Crick base pairing with a nucleic acid target). The MNAzyme only forms when the sensor arms of partzymes A and B hybridize adjacent to each other on the target. The substrate arms of the MNAzyme engage the reporter substrate, the cleavage of which is catalyzed by the catalytic core of the MNAzyme, formed by the interaction of the catalytic domains of partzymes A and B. The MNAzyme cleaves the substrate between a fluorophore and a quencher dye pair, thus generating signal. Cleavage of a DNA/RNA chimera (reporter substrate) is exemplified in the drawing. The term "MNAzyme" is also referred to as "multi-component nucleic acid enzyme". An MNAzyme may also comprise a stabilizing oligonucleotide, which provides stability of the MNAzyme by interacting with an assembly facilitator or substrate. It is apparent that formation of an MNAzyme requires the assembly of at least the partzyme components with the target (or assembly facilitator), as well as the binding of a reporter substrate, for catalytic activity to be detectable, and that the absence of any of these components will result in a lack of catalytic activity.

The reporter substrate used with the MNAzymes can be labeled by any of a large variety of means including, for example, fluorophores (with or without one or more additional components, such as quenchers), radioactive labels, labeling with biotin (e.g. biotinylation) or chemiluminescent labels. Reporter substrates for catalytic nucleic acids may also include protein or nucleic acid enzymes, for example, covalently attached to their termini.

The reporter substrates used with the MNAzymes may be generic reporter substrate systems, which allow rapid assay development by allowing facile design changes to create new MNAzymes which recognize different targets.

The substrate arm portion and the catalytic core portion of the partzymes may remain unchanged, with changes only to the sensor arm portion of one or more partzymes required for new targets. Generic substrate sequences are provided and the same substrate can therefore be incorporated in assays for many different targets. Further, the same substrate can be incorporated into the methods in various embodiments herein, including assays where the substrate is free in solution or is tethered or attached to a support. A series of generic substrates can be used in a multiplex reaction allowing simultaneous detection of multiple targets. MNAzyme strategies using generic substrates offer a major advantage over technologies such as TaqMan® or Beacons which require the design and use of probes specific for each new target.

As described in more detail below, MNAzymes have an advantageous property in certain embodiments of being able to utilize a universal or generic reporter substrate. Such a substrate is shown in FIG. 2 in a presently preferred configuration wherein the reporter substrate comprises both a detectable portion and a quencher portion. The quencher portion is adapted to diminish or eliminate a detectable signal from the detectable portion of the substrate until the MNAzyme cleaves the substrate. For example, the quencher portion may comprise "Black Hole Quencher 1" (BHQ1) or "Black Hole Quencher 2" (BHQ2). Thus, the MNAzyme cleaves the reporter substrate between the detectable portion and the quencher portion allowing the two portions to separate in solution, thereby allowing the detectable signal to appear or increase as the quencher portion is distanced from, or effectively removed from the local environment of the detectable portion.

The use of the generic or universal reporter substrate is enabled through the design of the MNAzyme's component partzymes. By altering only the sensor arms of the partzymes, but by leaving the substrate arms unchanged, a large variety of MNAzymes specific for each of a plurality of targets can be designed all of which utilize a universal reporter substrate for detection. The skilled artisan will appreciate the advantages that this offers in terms of eliminating the need for customized or unique substrates for each target. Each new target requires only one or more changes in one or more of the sensor arm portions; the substrate arm portion and the catalytic core portion can remain constant. Thus, a single reporter substrate can be used for a single target using an MNAzyme, and multiple targets in a series of assays using altered MNAzymes. A plurality of reporter substrates allows multiplexing to detect multiple targets in a single assay using multiple MNAzymes, one for each target. Such multiplexed methods of using MNAzymes are readily accomplished in solution or with attachment to a support system. It is contemplated herein that multiplexed assays can thus be accomplished in systems involving attaching one or more of the reporter substrate, or the MNAzyme partzymes or assembly facilitator, or additional enzyme activities, to a support as described herein.

Substrates can be modified by an MNAzyme thereby providing a detectable effect. In the detection process, the reporter substrate modification by an MNAzyme may involve, for example, cleavage, ligation, porphyrin metallation, and formation of carbon-carbon bonds, ester bonds or amide bonds. As a consequence of the reporter substrate modification by an MNAzyme, a detectable effect is generated and the magnitude of the effect may therefore be indicative of the quantity of the target sought to be measured. The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, UV, visible light or infra red spectroscopy, enzymatic methods or any combination thereof.

MNAzymes may contain one or more substitutions such as analogues, derivatives, modified or altered bases, ribonucleotides, alterations of the sugar or phosphate backbone, various deletions, insertions, substitutions, duplications or other modifications, or any combination of these, well known to those skilled in the art. Such modifications, substitutions, deletions, insertions, etc may be made in the sensor and/or substrate arms and/or in the catalytic core portions such that the molecule retains catalytic activity. Substitutions and modifications to arms that bind the substrate or assembly facilitator may be well tolerated and in fact are the basis of allowing tailoring of the molecules to different substrates/assembly facilitators. For example, modification of the sensor arms will allow tailoring to different assembly facilitators, while modification of the substrate arms will allow tailoring to different substrates.

The skilled artisan will appreciate that MNAzymes comprise either deoxyribonucleotides or ribonucleotides, or even both. Those MNAzymes comprising at least one and more preferably, all, deoxyribonucleotide component oligonucleotides are presently preferred. Also preferred are those MNAzymes comprising at least one deoxyribonucleotide base, or its analogue, within the catalytic core of the MNAzyme. Even more preferred are those embodiments where such a base is required for catalytic activity.

A basic example of a MNAzyme structure is depicted in FIG. 2. The structure shown comprises partzyme A and partzyme B which have base-paired with an MNAzyme assembly facilitator molecule, shown here simply as Target. Partzymes A and B by interacting with Target, have allowed the catalytic core to come into close proximity and thereby form. The substrate arms of the MNAzyme have interacted with and base-paired with a substrate, here Reporter Substrate. Thus the MNAzyme has self-assembled and this process is facilitated through the presence of the MNAzyme assembly facilitator molecule Target. In the absence of Target, no MNAzyme will form. Modification (in this case, cleavage) of the substrate is catalyzed by the catalytic core of the MNAzyme at the MNAzyme Cleavage Site within the substrate denoted by the vertical arrow. The substrate in this particular embodiment of the invention comprises a detectable portion having a detectable signal, for example fluorophore F, and a quencher portion having a quenching effect on the detectable signal F through the action of quencher Q. Upon cleavage at the MNAzyme Cleavage Site, there is a substantial increase in detectable signal, here fluorescence, which is readily detected or quantified.

More specifically, the partzyme A and partzyme B, shown in FIG. 2, each comprise a substrate arm portion, a catalytic core portion, and a sensor arm portion. In the presence of a target, the sensor arm portions of partzyme A and partzyme B can begin to hybridize to, and base pair with complementary portions of the target, for example a DNA or RNA sequence. Upon contacting the target in this fashion, the MNAzyme self-assembles forming a catalytic core, which can modify a substrate which is bound by the substrate arms. Preferably the presence of the MNAzyme is detected through the detection or measurement of its catalytic activity. The substrate arms of the thus assembled MNAzyme can engage a substrate, for example the reporter substrate shown in FIG. 2, through the interaction of the complementary sequences on the substrate arms and the substrate. Once the substrate is so engaged with the substrate arms, the catalytic core can promote the modification (eg. cleavage) of the substrate, which can in turn be measured or detected, directly or indirectly.

Multiple MNAzymes are useful in the present invention as they allow detection of related sequences differing by as little as a single nucleotide. Similarly, a unique reporter substrate is required to detect each of the several targets. In some cases, to multiplex the method requires the use of a distinct or unique detectable signal for each reporter substrate to facilitate the design of the method.

The target nucleic acid can be amplified in accordance with a procedure for amplifying that nucleic acid (i.e. DNA or RNA). Preferably, standard methods of in vitro amplification are used. The amplicons generated during the amplification serve as targets for an MNAzyme, thus MNAzyme activity is indicative of the presence of the target. The skilled artisan will appreciate that such monitoring can be conducted in a single vessel under conditions that permit both the amplification and the MNAzyme assembly and catalytic activity, or the MNAzyme assay can be conducted subsequent to, or at time points throughout the amplification, by removing samples at the end or during the course of the amplification reactions.

The method for detecting the presence of at least one target or assembly facilitator may further comprise providing at least a third and fourth oligonucleotide component, wherein said at least third and at least fourth oligonucleotide component are capable of self assembling in the presence of at least one additional target or assembly facilitator to form at least one additional catalytically active MNAzyme, and wherein at least one additional reporter substrate is present in the sample, said additional reporter substrate is capable of being modified only by the additional MNAzyme, wherein said modification provides said additional detectable effect.

Standard curves of threshold cycle (Ct) values over time for the target(s) are obtained and plotted onto the standard curves, generally obtained from a control or housekeeping gene, and the proportion of a given target in the viral population or in a given environment is visualized and calculated.

The protocols and products of the present invention may be used for diverse diagnostic, clinical, toxicological, research and forensic purposes including, drug discovery, designing patient therapy, drug efficacy testing, and patient management. The present methods may be used in combination with other assays. The results may be implemented in computer models and databases.

Additionally, the protocols and products of the present invention also allow monitoring of the effect of anti-RSV compounds on viral load.

DEFINITIONS

The terms "assembly facilitator molecule", "assembly facilitator", "MNAzyme assembly facilitator molecule", "facilitator" and "MNAzyme assembly facilitator" as used herein refer to entities that can facilitate the self-assembly of component partzymes to form a catalytically active MNAzyme. In preferred embodiments an assembly facilitator is required for the self-assembly of an MNAzyme. An assembly facilitator in some embodiments comprises a target such as a nucleic acid or non-nucleic acid analyte. Assembly facilitator molecules may comprise one or more regions or molecules that may pair with, or bind to, one or more oligonucleotide "partzymes," which constitute components or portions of an "MNAzyme". It is not required that the assembly facilitator interact with, pair with, or bind to each component partzyme or oligonucleotide provided that it interacts with, pairs with, or binds to, at least one of the component partzymes of an MNAzyme. As used herein, MNAzyme assembly facilitator molecules are intended to encompass the broadest range of constituents, which can facilitate self-assembly of an MNAzyme. In some embodiments, an assembly facilitator may comprise a nucleic acid. In other embodiments, an assembly facilitator may comprise any cell or any portion thereof, for example, any eukaryotic or prokaryotic cell, a virus, prion, yeast or fungus, or any other molecule, for example, including but not limited to a protein, polypeptide, peptide or nucleic acid. In other embodiments, an assembly facilitator may comprise a virus, prion, yeast or fungus, or any other molecule, for example, including but not limited to glycoproteins, lipids, lipoproteins, entire organisms, cells, viruses, bacteria, archaea, fungi, antibodies, metabolites, pathogens, toxins, contaminants, poisons, small molecules, polymers, metal ions, metal salts, prions or any derivatives, portions or combinations thereof.

The term "target" as used herein includes any natural or synthetic entity, constituent or analyte, which is sought to be detected, identified or quantified by a particular MNA zyme(s). Targets therefore encompass the broadest range of detectable entities, constituents or analytes for which methods of sensitive detection, identification and/or quantification are desirable. In some embodiments, a target comprises an assembly facilitator. Some exemplary targets include, but are not limited to, protein, polypeptide, peptide or nucleic acid, glycoproteins, lipids, lipoproteins, entire organisms, cells, viruses, bacteria, archaea, yeast, fungi, antibodies, metabolites, pathogens, toxins, contaminants, poisons, small molecules, polymers, metal ions, metal salts, prions or any derivatives, portions or combinations thereof. Other targets are also contemplated for use herein.

The terms "substrate", "substrate molecule" and "chemical substrate" as used herein include any molecule which is capable of being recognized, and acted upon or chemically modified by a catalytic molecule. In particular embodiments, a substrate may be recognized and modified by an enzyme. In other embodiments, a substrate may be recognized and modified by a catalytic nucleic acid molecule. The chemical modification of a substrate can be measured by the appearance of, or increase in, a product of the modification reaction, or by the disappearance of, or decrease in, a substrate of the modification reaction(s). A particular catalytic molecule may recognize one or more different substrate molecules provided each substrate molecule has at least a minimum structure, which is recognizable for catalytic activity by the catalytic molecule.

A "reporter substrate", "reporter probe" or "reporter probe substrate" as used herein is a substrate that is particularly adapted to facilitate measurement of either the disappearance of a substrate or the appearance of a product in connection with a catalysed reaction. Reporter substrates can be free in solution or bound (or "tethered"), for example, to a surface, or to another molecule. A reporter substrate can be labelled by any of a large variety of means including, for example, fluorophores (with or without one or more additional components, such as quenchers), radioactive labels, labelling with biotin (e.g. biotinylation) or chemiluminescent labels. Reporter substrates for catalytic nucleic acids may also include protein or nucleic acid enzymes, for example, covalently attached to their termini.

As used herein, the terms "partzyme", "component partzyme" and "component oligonucleotide" refer to a DNA-containing or RNA-containing or DNA-RNA-containing oligonucleotide, two or more of which, only in the presence of a MNAzyme assembly facilitator molecule, can together form an "MNAzyme." In certain preferred embodiments, one or more component partzymes, and preferably at least two, may comprise three regions or domains: a "catalytic" domain, which forms part of the MNAzyme's catalytic core that catalyzes a chemical modification; a "sensor arm" domain, which may associate with and/or bind to an assembly facilitator (e.g. a target); and a "substrate arm" domain, which may associate with and/or bind to a substrate. A depiction of these regions or domains can be seen, for example, in FIG. 2. A partzyme may comprise one or more molecules.

| Abbreviations | |
|---|---|
| MNAzyme : | multi-component nucleic acid enzyme, or multipartite nucleic acid enzyme; |
| DNAzyme : | deoxyribonucleic acid enzyme; |
| RNAzyme : | ribonucleic acid enzyme, or ribozyme; |
| PCR : | polymerase chain reaction; |
| dH$_2$O : | deionized distilled water; |
| F : | fluorophore; |
| Q : | quencher; |
| JOE or 6-JOE : | 6-carboxy-4',5'-dichloro-2',7'-dimethoxyfluorescein; |
| FAM or 6-FAM : | 6-Carboxyfluorescein; |
| BHQ1 : | Black Hole Quencher 1; |
| BHQ2 : | Black Hole Quencher 2. |

FIGURES

FIG. 1 is a diagnostic workflow for RSV viral load determination.

FIG. 2 is a depiction of an exemplary design for an MNAzyme, wherein substrate arm portions (A) of partzymes A and B bind to a Reporter substrate, to which is attached a fluorescent tag (left) and a quencher (right). Catalytic core portions (C) are located between substrate arm portions (A) and sensor arm portions (B). Upon binding of sensor arm portions (B) to a Target, the Reporter substrate is cleaved at the MNAzyme Cleavage Site, thereby increasing fluorescence.

Figure 3:
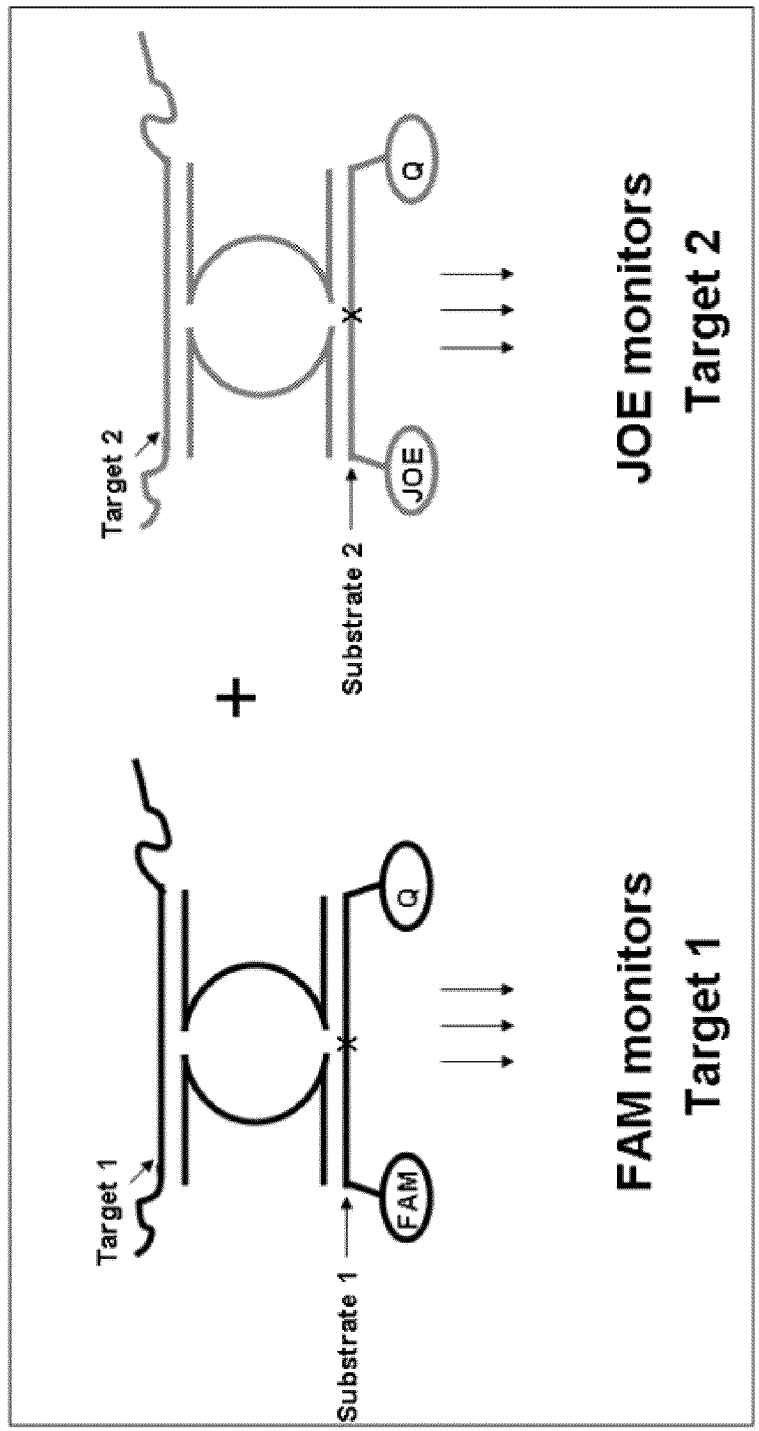

FIG. 3: Schematic representation of an exemplary multiplex analysis of multiple targets: Two or more targets can be simultaneously detected using two or more substrates, each specific for one MNAzyme. Substrates are preferably labeled with different fluorophores. In this example, Target 1 can be detected by monitoring the increase in FAM fluorescence and Target 2 can be detected by monitoring the increase in JOE fluorescence. Q: quencher; FAM, JOE: fluorophores.

FIG. 4: Schematic representation of the External Quantification Control sequences cloned in the TOPO-TA vector (Invitrogen, Merelbeke): EQC-A (A) and EQC-B (B). The vectors indicate the T7 promotor and the flanking primers used to generate the amplicon that was cloned. Also shown are the two primers used during the q-RT-PCR assay in each vector as well as the location of the NdeI restriction site used to linearize the vectors before transcription.

Figure 5A:
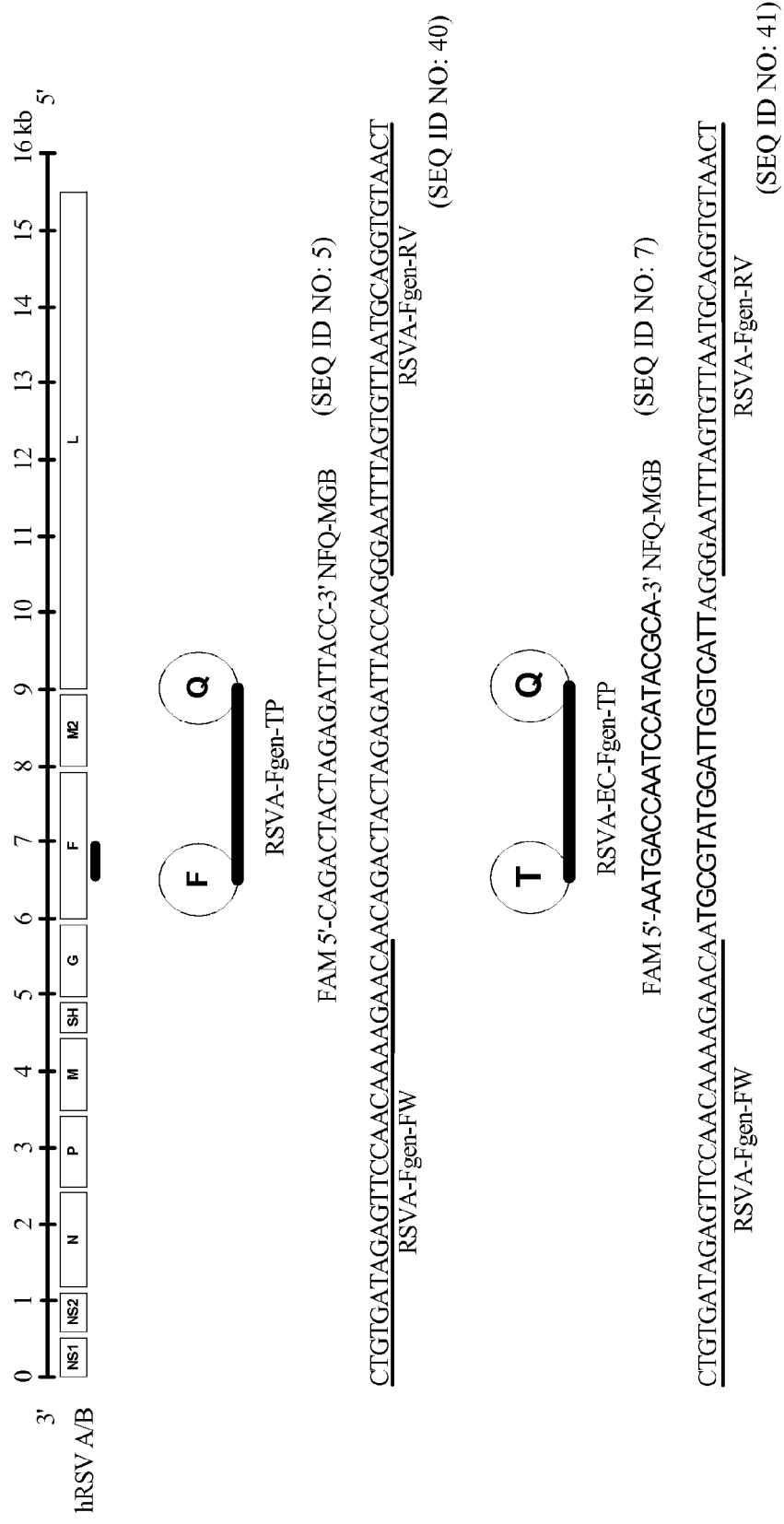

FIG. 5a/b: Schematic representation of the internal extraction control sequences. The q-RT-PCR amplification uses an RSV-A and RSV-B conserved and specific sequence in the RSV genome. These sequences are located in the F-gene for RSV-A (1) and the N-gene for RSV-B (3). The primers to amplify the RSV RNA or the RSV internal extraction control are identical per sub-strain: The sequences in between the primers are probe-specific: RSV-A RNA =RSVA-Fgen-TP probe (1) (SEQ ID NO: 5), RSV-A internal extraction control =RSVA-EC-Fgen-TP probe (2) (SEQ ID NO: 7); RSV-B RNA =RSVB-Ngen-TP probe (3) (SEQ ID NO: 6), RSV-B internal extraction control =RSVB-EC-Ngen-TP probe (4) (SEQ ID NO: 8).

FIG. 6: Schematic representation of the Internal Extraction Control (IEC) sequences cloned in the TOPO-TA vector (Invitrogen, Merelbeke): pIEC-A (A) and pIEC-B (B). The vectors indicate the T7 promotor, the two primers and the probe location for each vector as well as the location of the ApaLI restriction sites used to linearize the vectors before transcription.

The following non-limiting examples help to illustrate the principles of the invention.

EXAMPLES

Example 1

Sputum and NPW was received from various sources (REGA, Leuven, Belgium; O. L. V. Ziekenhuis, Aalst, Belgium). Sputa and NPW samples used in these experiments when not infected with RSV were spiked with an RSV virus stock (RSV-A: RSV-GFP 011828) whenever applicable.

Additionally a Dyspomix (Wilten Instruments, Cat nr 900.021.00, Berchem, Belgium), an AFA (Covaris, Hoddesdon, UK) and an ABI9700HT (Applied Biosystems, Calif., USA) were used during the course of these experiments.
Sample Processing in Preparation of Automated RNA Extraction A method was developed for the preparation of different RSV samples for automated RNA extraction (see FIG. 1 for the schematic diagnostic workflow).

Different kinds of processing could occur with different kinds of samples (as described in Table 1).

Samples were stored in-house at −80° C. The weight of the frozen samples was determined while still frozen, 1 volume of PBS/10% DTT was added to the samples with a minimal final volume of 2.2 ml (in Becton Dickinson 14 ml polypropylene round-bottom tube, ref number 352059 (25 per bag, sterile)). Samples with an estimated initial volume larger than 1.5 ml were first transferred to a 50 ml tube before addition of one volume PBS/10% DTT by slightly warming the 15 ml tube until the frozen sample could be slid into the 50 ml Falcon tube (Red cap). The frozen sample/PBS-10% DTT was placed in the Covaris S2 instrument and processed with SonoLAB Single v2.4.3 with the following settings:

Mode=Power Tracking, Number of Cycles=10, Bath Temperature Limit=15° C.

Treatment 1: "Duty Cycle"=20%, "Intensity"=10 and "Cycles/Burst"=100 for 30 s.

Treatment 2: "Duty Cycle"=0.1%, "Intensity"=0.1 and "Cycles/Burst"=50 for 10 s.

Mostly one (1) cycle was sufficient to dissolve the sample, if not, extra cycles were added as needed.

The cooling of the Covaris was set at 1° C.

After Covaris treatment, 4 initial sample volumes of Lysis buffer (EasyMAG, BioMérieux) were added and incubated for 10 minutes.

The Covaris S2 instrument as described above can be found on the website of Covaris viz www.covarisinc.com. In summary the Covaris process produces a controlled acoustic field inside a sealed vessel. The process is based on a computer-controlled, focused acoustic energy technology. The Covaris Adaptive Focused Acoustics (AFA) process works by sending acoustic energy wave packets from a dish-shaped transducer that converges and focuses to a small-localized area (it is sometimes visualized as a vibrating loudspeaker cone). At this focal point, the energy density may be controllably focused into the sample of interest which has proven to be beneficial to numerous applications of sample preparation. Essentially, the process enables mechanical energy to be applied to a sample without directly contacting the sample.

An advanced Covaris instrument comprises a so-called intensifier which is attached to the transducer producing the waves. Said waves starting from the centre of the concave intensifier are reflected by the cone and the obtained vertical waves produces an extra heating at the bottom of the vessel.
Automated RNA Extraction The RNA was extracted using the EasyMAG platform (BioMérieux) according to the instructions provided by the supplier with the following adaptation: 3 ml of the lysed sample volume was used (No lysis dispensing on the EasyMAG), per 8 samples to be extracted: 110 µl IEC-B (internal extraction control for RSV-B, stored in −80° C.) was mixed with 440 µl EasyMAG Buffer 3 and 55000 µl magnetic beads. A total of 125 µl of this mix was dispensed in separate wells using the pre-programmed settings number 2 of the EasyMAG dispensing pipet. Using the pre-programmed set-

TABLE 1

Overview of different sample types and different preparation methods.

| | Sputum (human) | NPW (human) | Bal (mouse) fluid | Virus Culture (Supernatant) | Virus Culture (Cell fraction) | Lung tissue (rat) |
|---|---|---|---|---|---|---|
| Covaris S2 | Yes | Yes | Yes | Yes | Yes | No |
| Dyspomix | Yes | Yes | Yes | Yes | Yes | Yes |
| EasyMAG | No | Yes | Yes | Yes | No | No |

NPW: Nasopharyngeal Wash; BAL: Bronchoalveolar Lavage tings number 3 of the EasyMAG dispensing pipet 100 μl of this mix was added to each sample. Elution occurred in 110 μl (Buffer 3, EasyMAG). As soon as the extraction was completed, the q-RT-PCR technology or MNAzyme technology was performed as described in Example 2 (A) and (B) respectively. The remainder of the RNA was stored at −80° C.

Two possibilities were used for quantification, either q-RT PCR using Taqman technology (q-RT PCR technology and Taqman probes) or the MNAzyme technology.

For a detailed explanation of q-RT-PCR technology specific reference is made to EP 543, 942 filed by F. Hoffmann-La Roche AG, Switzerland, while the MNAzyme technology is explained in great detail in patent application PCT/AU2006/001473 filed by Johnson & Johnson Research Pty Limited, Australia) and both are herewith incorporated by reference for detailed explanation of both technologies.

Example 2

(A) Use of q-RT PCR Technology and Taqman Probes for the Quantification of RSV-A and RSV-B Viral Strains and a Control Nucleic Acid Sequences Via Monoplex Real Time PCR Probes and Primers:
The primers for the RSV-A q-RT-PCR amplification (and hence also pIEC-A) were:

| Oligonucleotide | Sequence | |
|---|---|---|
| RSV-A-Fgen-FW | 5'-CTGTGATAGA RTTCCAACAA AAGAACA-3' | SeqID No. 1 |
| RSV-A-Fgen-RV | 5'-AGTTACACCT GCATTAACAC TAAATTCC-3' | SeqID No. 2 |

The primers for the RSV-B q-RT-PCR amplification (and hence also pIEC-B) were:

| Oligonucleotide | Sequence | |
|---|---|---|
| RSV-B-Ngen-FW | 5'-GGCTCCAGAA TATAGGCATG ATTC-3' | SeqID No. 3 |
| RSV-B-Ngen-RV | 5'-TGGTTATTAC AAGAGCAGCT ATACACAGT-3' | SeqID No. 4 |

The probe for RSV-A was:

| Probe | Sequence | |
|---|---|---|
| RSV-A-Fgen-TP | FAM 5'-CAGACTACTAGAGATT ACC-3' NFQ-MGB* | SeqID No. 5 |

*NFQ-MGB: Non-Fluorescent Quencher - Minor Groove Binding Sequence

The probe for RSV-B was:

| Probe | Sequence | |
|---|---|---|
| RSV-B-Ngen-TP | FAM 5'-TATCATCCCAC AGTCTG-3' NFQ-MGB | SeqID No. 6 |

The probe for pIEC-A was:

| Probe | Sequence | |
|---|---|---|
| RSV-A-EC-Fgen-TP | FAM 5'-AATGACCAATCCATA CGCA-3' NFQ-MGB | SeqID No. 7 |

The probe for pIEC-B was:

| Probe | Sequence | |
|---|---|---|
| RSV-B-EC-Ngen-TP | FAM 5'-TACCGTACTCTAG CCTA-3' NFQ-MGB | SeqID No. 8 |

For each sample, three q-RT-PCR mixes were prepared in duplicate:
RSV-A, RSV-B and IEC

| RSV-A, RSV-B and IEC | | | | | |
|---|---|---|---|---|---|
| Samples | 1 | | | | |
| Reaction Vol. (μl) | 30 | | | | |

| | | Concentration | | Volume for (μl) | |
|---|---|---|---|---|---|
| Mix item | Unit | Stock | Final | 1 sample | X samples |
| Rnase free water | | | | 0.77 | 2.31 |
| Yeast tRNA | ng/ml | 10000 | 120 | 0.360 | 1.08 |
| 2x Reaction buffer | X | 2.00 | 1.000 | 15.000 | 45.00 |
| Euroscript RT | kU/ml | 50.00 | 0.250 | 0.150 | 0.45 |
| Probe RSV | μM | 25.00 | 0.100 | 0.120 | 0.36 |
| RSV primer FW | μM | 20.00 | 0.900 | 1.350 | 4.05 |
| RSV primer RV | μM | 20.00 | 0.900 | 1.350 | 4.05 |
| MgCl$_2$ | μM | 50.00 | 1.500 | 0.900 | 2.70 |
| Total Volume Mix (μl) | | | | | 60.00 |
| Volume Mix/Tube (μl) | | | | 20.00 | |
| Total RNA RSV-A | | | | 10.00 | |

When all components were added to the plate, the plate was sealed with an Optical Adhesive Cover (ABI) and centrifuged for 1 minute at 1500 rpm. Before processing on the ABI7900HT, the plate was covered with a MicroAmp™ Snap-On Optical Film Compression Pad (ABI).

Thermal Profile was:
"Stage 1" reverse transcriptase reaction: 48° C., 30 minutes
"Stage 2" activation of polymerase: 95° C., 10 minutes
"Stage 3": 45 repeats:
95° C. denaturation, 15 seconds
60° C. elongation, 1 minute Construction of the External Quantification Control (EQC) for the RSV q-RT PCR Assay In order to define the dynamic range of the q-RT-PCR assay, external quantification controls were constructed. This included:
Design of the following plasmid constructs containing:
The sequence situated between the forward (EQC-RSV-A-FW) and reverse primer (EQC-RSV-A-RV) covering a region of RSV-A of 1004 base pairs including the region where the RSV-A q-RT-PCR assay primers and probes anneal. This construct is labeled as external quantification control RSV-A (pEQC-A).
The sequence situated between the forward (EQC-RSV-B-FW) and reverse primer (EQC-RSV-B-RV) covering a region of RSV-A of 1399 base pairs including the region where the RSV-B q-RT-PCR assay primers and probes anneal. This construct is labeled as external quantification control RSV-B (pEQC-B).

Primers and Probes

The primers ordered the pEQC-A (EQC-RSV-A-FW, EQC-RSV-A-RV and EQC-RSV-A-RVret) and pEQC-B (EQC-RSV-B-FW, EQC-RSV-B-RV and EQC-RSV-B-RVret) constructs are described hereunder.

```
Oligonucleotide

EQC-RSV-A-FW     5'-AATCAAAATAAACTCTGGGGC-3'  bp 5631-5651*  SeqID No. 9

EQC-RSV-A-RV     5'-GTTGGTTGTACATAGAGGGG-3'   bp 6634-6615*  SeqID No. 10

EQC-RSV-A-RVret  5'-TACATGTTTCAGCTTGTGGG-3'   bp 6734-6715*  SeqID No. 11

EQC-RSV-B-FW     5'-ATATTTATCAATCATGGCGGG-3'  bp 908-928**   SeqID No. 12

EQC-RSV-B-RV     5'-CTACATCATCTTCTTTGGGG-3'   bp 2306-2286** SeqID No. 13

EQC-RSV-B-RVret  5'-GTGCCAGATGTTATCGGGC-3'    bp 2524-2507** SeqID No. 14

*Positions are base on the Long strain (AY911262, RSV-A)
**Positions are based on AY353550 (RSV-B)
```

RSV Samples

For this experiment an aliquot of RSV-A-GFP (GST011828) and RSV-B-P3-Hep2 (REGA) virus stock were used.

RNA Extraction and Amplification of Desired RSV Genome Fragments

An RSV-A-GFP (GST011828) and RSV-B-P3-Hep2 (REGA) virus stock was extracted on the EasyMAG: 1000 µl input, 55 µl output. The RNA was subsequently submitted to an RT-hemi-nested PCR amplification. The PCR mixes and conditions are specified hereunder.

Overview of the different (RT) PCR amplification mixes and conditions to generate the hemi-nested amplification products for RSV-A (1004 bp) and RSV-B (1399 bp). The exact primer sequences are mentioned above.

RT-PCR

| # Samples | 1 |
| --- | --- |
| Reaction Vol. (µl) | 35 |

| Mix Item | Concentration | | | Volume for (µl) | |
| --- | --- | --- | --- | --- | --- |
| | Unit | Stock | Final | 1 sample | x samples |
| Rnase Free water | | | | 6.10 | 12.20 |
| 2x Reaction buffer HiFi | X | 2.00 | 1.000 | 17.50 | 35.00 |
| Primer FW | µM | 20.00 | 0.200 | 0.35 | 0.70 |
| Primer RVret | µM | 20.00 | 0.200 | 0.35 | 0.70 |
| Superscript™ III HiFi | U/µl | 100.00 | 2.000 | 0.70 | 1.40 |
| Total Volume Mix (µl) | | | | 25.00 | 50.00 |
| Total Volume RNA (µl) | | | | 10.00 | | thermal cycling

| step | temp. (° C.) | time | cycles |
| --- | --- | --- | --- |
| 1 | 53 | 30' | |
| 2 | 94 | 2' | |
| 3 | 92 | 15" | 40 |
| 4 | 55 | 30" | |
| 5 | 68 | 1'30" | |
| 6 | 68 | 7' | |
| 7 | 4 | hold | |

Heminested

| # Samples | 1 |
| --- | --- |
| Reaction Vol. (µl) | 50 |

| Mix Item | Concentration | | | Volume for (µl) | |
| --- | --- | --- | --- | --- | --- |
| | Unit | Stock | Final | 1 sample | x samples |
| Rnase Free water | | | | 39.17 | 78.34 |
| PCR Buffer (15 mM MgCl$_2$) | X | 10.00 | 1.000 | 5.00 | 10.00 |
| dNTPs | mM | 25.00 | 0.200 | 0.40 | 0.80 |
| Primer FW | µM | 20.00 | 0.200 | 0.50 | 1.00 |
| Primer RV | µM | 20.00 | 0.200 | 0.50 | 1.00 |
| Expand ™HF PCR | U/µl | 3.50 | 0.030 | 0.43 | 0.86 |
| Total Volume Mix (µl) | | | | 46.00 | 92.00 |
| Total Volume RT-PCR mix (µl) | | | | 4.00 | | thermal cycling

| step | temp. (° C.) | time | cycles |
| --- | --- | --- | --- |
| 1 | 94 | 2 min | |
| 2 | 94 | 15" | 35 |
| 3 | 60 | 30" | |
| 4 | 68 | 1' | |
| 5 | 68 | 7' | |
| 6 | 4 | hold | |

TOPO-TA Cloning

The obtained PCR fragments were cloned using the TOPO TA cloning kit (Invitrogen, Merelbeke, Belgium) following the manufacturer's instructions. Briefly, 4 µl PCR product (unpurified) was mixed with 1 µl salt solution and 1 µl vector.

The ligation reaction was transformed into TOP10 chemically competent E. coli cells following the manufacturer's instructions.

After growing the E. coli cultures overnight, 10 colonies per construct (pEQC-A and pEQC-B) were transferred to liquid LB/Ampicillin medium, grown overnight and a miniprep (Qiagen, Hilden, Germany) was performed. Final volume=50 µl, concentration not measured.

Sequencing

A total of 0.75 µl of the generated DNA was submitted to sequencing. Sequencing was done using the Big Dye Terminator (BDT) Cycle Sequencing Kit v3.1 (Cat n°. 4337457, Applied Biosystems, Calif., USA).

The mix composition of each well is indicated in below table. The sequencing reactions were performed using the primer set
"T3" (5'-ATTAACCCTCACTAAAGGGA-3') (SeqID No. 15) and
"T7" (5'-TAATACGACTCACTATAGGG-3') (SeqID No. 16) which are located on the TOPO-TA vector.

The sequencing PCR was done using the 9800 Fast Thermal Cycler (Applied Biosystems (ABI), Cat. nr. 4356204, Calif., USA). The PCR conditions were 96° C. for 5 seconds, 50° C. for 5 seconds, 60° C. for 1 minute and 15 seconds and this for 25 cycles in total followed by a final hold at 12° C.

TABLE

The mix composition of a single sequencing reaction, with a final volume of 5.75 µl.

Sequencing Mix preparation (µl):

|  | 1 well | xwells 20 |  |
|---|---|---|---|
| BDT | 0.25 | 5.25 | µl |
| DB | 1.25 | 26.25 | µl |
| Water | 1.50 | 31.50 | µl |
| Primer* | 2.00 | 42.00 | µl |
| tot mix | 5.00 | 105.00 | µl |
| amplicon | 0.75 |  |  |

Speed PCR program:

| 96° C. | 5" | # cycli |
|---|---|---|
| 50° C. | 5" | 25 |
| 60° C. | 1'15" |  |
| 12° C. | hold |  |

(*T7 or T3 sequencing primer was used).
"BDT" = Big Dye Terminator,
"DB" = Dilution Buffer

In Vitro RNA Transcription

One correct clone of each EQC construct (Clone 6 for EQC-A and Clone 3 for EQC-B) was linearized using the restriction enzyme NdeI (FIGS. 4 A & B).

Restriction enzyme digestion proceeded at 37° C. for 3 hours using restriction enzyme buffer 4. The reactions were stopped by incubation at 65° C. (20 minutes) and purified. To the restriction digest mix, 1/20 volumes of 0.5M EDTA (1 µl), 1/10 volumes of NaOAC (2 µl) and 2 volumes of EtOH (40 µl) were added. The mixture was placed at −20° C. for minimum 15 minutes, and then spun for 15 minutes at maximum speed. The supernatant was discarded and the pellet was dissolved in 50 µl TE buffer. The linearized constructs were then transcribed using the MEGAshortscript™ T7 Kit (Ambion, Cat. nr. 1354, Tex., USA). The reaction mixtures were incubated at 37° C. for 4 hours. The total length of the transcribed RNA was predicted to be 1250 (EQC-A) and 1600 (EQC-B) nucleotides. Multiple parallel reactions were set up for each EQC.

DNA Removal

The transcription mixtures were treated with TURBO DNase™ (2 µl added to transcription mix, Ambion, Cat. Nr. 2238, Tex., USA). The DNase treatment lasted for 1 hour at 37° C. in a final volume of 100 µl. The RNA was purified by means of an RNA extraction on the EasyMAG (BioMérieux) eluting in 100 µl The purified eluates were pooled resulting in a final volume of about 1 ml per EQC.

Real-time EQC Quantification

The purified transcripts were submitted to a real-time PCR quantification either in the presence or the absence of the RT enzyme. The mix compositions of the various mixes can be found hereafter:

| EQC-A | | | | | |
|---|---|---|---|---|---|
| # Samples | | | 1 | | |
| Reaction Vol. (µl) | | | 30 | | |
| | | Concentration | | Volume for (µl) | |
| Mix item | Unit | Stock | Final | 1 sample | X samples |
| Rnase free water | | | | 1.670 | 5.01 |
| Yeast tRNA | ng/ml | 10000 | 120 | 0.360 | 1.08 |
| 2x Reaction buffer | X | 2.00 | 1.000 | 15.000 | 45.00 |
| Euroscript RT | kU/ml | 50.00 | 0.250 | 0.150 | 0.45 |
| Probe RSV-A | µM | 25.00 | 0.100 | 0.120 | 0.36 |
| RSV-A primer FW | µM | 20.00 | 0.900 | 1.350 | 4.05 |
| RSV-A primer RV | µM | 20.00 | 0.900 | 1.350 | 4.05 |
| Total Volume Mix (µl) | | | | | 60.00 |
| Volume Mix/Tube (µl) | | | | 20.00 | |
| Total RNA | | | | 10.00 | |

| EQC-B | | | | | |
|---|---|---|---|---|---|
| # Samples | | | 1 | | |
| Reaction Vol. (µl) | | | 30 | | |
| | | Concentration | | Volume for (µl) | |
| Mix item | Unit | Stock | Final | 1 sample | X samples |
| Rnase free water | | | | 1.670 | 5.01 |
| Yeast tRNA | ng/ml | 10000 | 120 | 0.360 | 1.08 |

-continued

|  |  |  | | | |
|---|---|---|---|---|---|
| 2x Reaction buffer | X |  | 2.00 | 1.000 | 15.000 | 45.00 |
| Euroscript RT | kU/ml | 50.00 | 0.250 | 0.150 | 0.45 |
| Probe RSV-B | μM | 25.00 | 0.100 | 0.120 | 0.36 |
| RSV-B primer FW | μM | 20.00 | 0.900 | 1.350 | 4.05 |
| RSV-B primer RV | μM | 20.00 | 0.900 | 1.350 | 4.05 |
| Total Volume Mix (μl) | | | | | 60.00 |
| Volume Mix/Tube (μl) | | | | 20.00 | |
| Total RNA | | | | 10.00 | |

The program used on the ABI9700 HT real-time PCR equipment was 48° C. for 30 minutes, 95° C. for 10 minutes followed by 45 cycles of 95° C. for 15 seconds and 60° C. for 1 minute. For all experiments only FAM-labeled probes were used (Monoplex assays).

Reproducibility of EQC (Frozen Aliquots)

From the EQC RNA pools (evaluated for residual DNA content), dilution series were made over 8 logs (8 aliquots, diluted 1/10) with a total volume of 2500 μl. From these stocks aliquots were taken of 23 μl each and stored at −80° C. until processing occurred.

Sample Processing, an Example

In total 5 clinical samples were processed (Flow chart, see FIG. 1). All samples were transferred to a 15 ml falcon tube and PBS/1% DTT was added to a final volume of 2.2 ml. This mix was processed on the AFA (Covaris) for 60 seconds prior to the addition of 4 ml lysis buffer (EasyMAG, BioMérieux). From these 6.2 ml per sample, 3 ml was processed on the EasyMAG (BioMérieux) and the RNA was eluted in 110 μl of which 10 μl was processed in the q-RT-PCR in duplicate. The experiment was repeated once starting from extraction with the remaining 3 ml.

Results

PCR

The RT-Heminested PCR reactions were set up in duplo and both generated good results for each amplicon. The expected size for the RSV-A amplicon was 1004 bp and for RSV-B 1399 bp. These PCR amplified fragments were ligated in a TOPO-TA vector and transformed into competent E. coli. The transformants were grown overnight on solid LB/ampicillin plates. A total of 10 colonies were transferred to liquid LB/Ampicillin medium and again grown overnight. A miniprep (Qiagen, Hilden, Germany) was prepared from these cultures and the resulting DNA was submitted to sequencing.

Sequencing

Not all PCR fragments ligated in the same direction in the TOPO-TA vector. A total of 2 clones for pEQC-A and 6 clones for pEQC-B were cloned in the correct direction into the TopoTA vector. Of these clones, Clone 6 (pEQC-A) and Clone 3 (pEQC-B) were chosen for the in vitro transcription.

In Vitro Transcription

Clone 6 (pEQC-A) and Clone 3 (pEQC-B) were submitted to a restriction digest using NdeI and purified as described above. The linearized and purified constructs were submitted to an in vitro transcription (using the MEGAshortscript™ T7 Kit (Ambion)). The residual DNA was removed using the TURBO DNase™ (Ambion). The transcripts were purified by means of an RNA extraction on the EasyMAG (BioMérieux) as described above.

Real-time PCR Results

The pure transcripts were diluted 1/1000 and submitted to a real-time PCR quantification reaction with (dark blue signal) and without (light blue signal) RT enzyme to determine the residual DNA content of the transcripts. The 4-hour transcript of pEQC-A showed a difference of 12 Cts between the reaction performed without RT and the reaction performed in the presence of RT. The residual DNA in the RSV-B transcripts was comparable to that of pEQC-A with about 10 Cts difference between the reactions performed in the presence or the absence of the RT enzyme.

Both controls contain less than 1 DNA molecule in 1000 RNA molecules. This is acceptable to use as an RNA control.

Stability (Reproducibility) of Ct Value Determination on Dilution Series of EQC

Over several days and by different operators frozen EQC (A and B) dilution series were analyzed by means of q-RT-PCR quantification. The results of these tests (n=6) show a dynamic range of 6-7 logs. The repeated experiments indicated a good reproducibility with an average slope of −3.39 (EQC-A) and −3.33 (EQC-B), a Y-axis intercept of 42.56 (EQC-A) and 41.51 (EQC-B) and a correlation of 0.999 of the data points for both EQC-A and EQC-B. For EQC-A, 5/6 runs had a linear range of 7 logs. The mean Ct value of the lowest dilution (n=6) was 11.98511 (stdev 0.484211) and of the highest dilution was 35.90961 (stdev 0.988846) (n=5, for run 5 the highest dilution was not measured). For EQC-B 4/6 only had a linear range of 6 logs. The mean Ct value of the lowest dilution (n=6) was 10.98107 (stdev 0.569094) and of the highest common dilution (n=6) was 30.8342 (stdev 0.657034).

Interpretation of the Standard Curve, an Example

A total of 4 NPW samples and one sputum sample were processed. For both experiments also the external quantification controls EQC-A and EQC-B were taken along. Two settings were tested to investigate what the best interpretation mode was for the standard curves (i.e. what would allow to calculate "Ct value 1" of a sample in one experiment according to standard curve 1, and "Ct value 2" of that same sample in a second experiment according to standard curve 2 in such a way that both Ct values would be closest to each other): setting the threshold identical for all experiments or setting the Y-axis intercept identical for all experiments?

In a first setting, the threshold of the standard curves in both experiments was set to 0.1. As can be observed, none of the measurements deviated by more than 1 Ct. The mean of the differences was 0.56 Ct with a standard deviation of 0.39.

In another setting, it was tried to minimize the difference of the standard curves concerning the Y-axis intercept. As such, the threshold of the repeat experiment was modified to make the Y-axis intercept of the second EQC-A standard curve move closer to 42.43 (42.428). With this setting, one measurement differed more than 1 Ct (NPW 5: 1.04). The average of the differences however was only 0.47 with a standard deviation of 0.43.

CONCLUSION

Two vectors were constructed and sequenced. They both contained a part of the RSV genome (RSV-A 1004 bp and RSV-B 1399 bp). The purified DNase-treated transcripts were analyzed in the presence or the absence of the RT enzyme in a real-time PCR quantification assay. This indicated that for both EQCs, a suited RNA control transcript was obtained that contained less than 1 DNA molecule in 1000 RNA molecules.

Repeated experiments indicated that the EQC dilution series delivered stable, reproducible results over different days and different operators with a dynamic range of 6 to 7 logs.

The sequence of pEQC-A (clone 6) and pEQC-B (clone 3) respectively are depicted below.

```
Sequence of pEQC-A: (SeqID No. 17)
(Bold = primer sequence; underlined = probe sequence)
TGCACTGGCCAGGGGGATCACCATCCGTCGCCCCGGCGTGTCAATAATATCACTCTGTACATCCACAAAC

AGACGATAACGGCTCTCTCTTTTATAGGTGTAAACCTTAAACTGCCGTACGTATAGGCTGCGCAACTGTT

GGGAAGGGCGATCGGTGCGGGCCTCTTCGCTATTACGCCAGCTGGCGAAAGGGGATGTGCTGCAAGGCG

ATTAAGTTGGGTAACGCCAGGGTTTTCCCAGTCACGACGTTGTAAAACGACGGCCAGTGAATTGTAATAC

GACTCACTATAGGGCGAATTGAATTTAGCGGCCGCGAATTCGCCCTTAATCAAAATAAACTCTGGGGCAA

ATAACAATGGAGTTGCCAATCCTCAAAGCAAATGCAATTACCACAATCCTCGCTGCAGTCACATTTTGCT

TTGCTTCTAGTCAAAACATCACTGAAGAATTTTATCAATCAACATGCAGTGCAGTTAGCAAAGGCTATCT

TAGTGCTCTAAGAACTGGTTGGTATACTAGTGTTATAACTATAGAATTAAGTAATATCAAGGAAAATAAG

TGTAATGGAACAGATGCTAAGGTAAAATTGATAAACCAAGAATTAGATAAATATAAAAATGCTGTAACAG

AATTGCAGTTGCTCATGCAAAGCACAACAGCAGCAAACAATCGAGCCAGAAGAGAACTACCAAGGTTTAT

GAATTATACACTCAACAATACCAAAAAAACCAATGTAACATTAAGCAAGAAAAGGAAAAGAAGATTTCTT

GGTTTTTTGTTAGGTGTTGGATCTGCAATCGCCAGTGGCATTGCTGTATCTAAGGTCCTGCACTTAGAAG

GAGAAGTGAACAAGATCAAAAGTGCTCTACTATCCACAAACAAGGCCGTAGTCAGCTTATCAAATGGAGT

TAGTGTCTTAACCAGCAAAGTGTTAGACCTCAAAAACTATATAGATAAACAATTGTTACCTATTGTGAAT

AAGCAAAGCTGCAGAATATCAAATATAGAAACTGTGATAGAGTTCCAACAAAAGAACAAC<u>AGACTACTAG</u>

<u>AGATTACCA</u>GGGAATTTAGTGTTAATGCAGGTGTAACTACACCTGTAAGCACTTACATGTTAACTAATAG

TGAATTATTGTCATTAATCAATGATATGCCTATAACAAATGATCAGAAAAAGTTAATGTCCAACAATGTT

CAAATAGTTAGACAGCAAAGTTACTCTATCATGTCCATAATAAAAGAGGAAGTCTTAGCATATGTAGTAC

AATTACCACTATATGGTGTGATAGATACACCTTGTTGGAAATTACACACATCCCCTCTATGTACAACCAA

CAAGGGCGAATTCGTTTAAACCTGCAGGACTAGTCCCTTTAGTGAGGGTTAATTCTGAGCTTGGCGTAAT

CATGGTCATAGCTGTTTCCTGTGTGAAATTGTTATCCGCTCACAATTCCACACAACATACGAGCCGGAAG

CATAAAGTGTAAAGCCTGGGGTGCCTAATGAGTGAGCTAACTCACATTAATTGCGTTGCGCTCACTGCCC

GCTTTCCAGTCGGGAAACCTGTCGTGCCAGCTGCATTAATGAATCGGCCAACGCGCGGGGAGAGGCGGTT

TGCGTATTGGGCGCTCTTCCGCTTCCTCGCTCACTGACTCGCTGCGCTCGGTCGTTCGGCTGCGGCGAGC

GGTATCAGCTCACTCAAAGGCGGTAATACGGTTATCCACAGAATCAGGGGATAACGCAGGAAAGAACATG

TGAGCAAAAGGCCAGCAAAAGCCCAGGAACCGTAAAAAGGCCGCGTTGCTGGCGTTTTTCCATAGGCTCC

GCCCCCCTGACGAGCATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTGCCGCTTACCGGATAC

CTGTCCGCCTTTCTCCCTTCGGGAAGCGTGGCGCTTTCTCATAGCTCACGCTGTAGGTATCTCAGTTCGG

TGTAGGTCGTTCGCTCCAAGCTGGGCTGTGTGCACGAACCCCCCGTTCAGCCCGACCGCTGCGCCTTATC

CGGTAACTATCGTCTTGAGTCCAACCCGGTAAGACACGACTTATCGCCACTGGCAGCAGCCACTGGTAAC

AGGATTAGCAGAGCGAGGTATGTAGGCGGTGCTACAGAGTTCTTGAAGTGGTGGCCTAACTACGGCTACA

CTAGAAGGACAGTATTTGGTATCTGCGCTCTGCTGAAGCCAGTTACCTTCGGAAAAAGAGTTGGTAGCTC

TTGATCCGGCAAACAAACCACCGCTGGTAGCGGTGGTTTTTTTGTTTGCAAGCAGCAGATTACGCGCAGA

AAAAAGGATCTCAAGAAGATCCTTTGATCTTTTCTACGGGGTCTGACGCTCAGTGGAACGAAAACTCAC

GTTAAGGGATTTTGGTCATGAGATTATCAAAAAGGATCTTCACCTAGATCCTTTTAAATTAAAAATGAAG
```

-continued
```
TTTTAAATCAATCTAAAGTATATATGAGTAAACTTGGTCTGACAGTTACCAATGCTTAATCAGTGAGGCA

CCTATCTCAGCGATCTGTCTATTTCGTTCATCCATAGTTGCCTGACTCCCCGTCGTGTAGATAACTACGA

TACGGGAGGGCTTACCATCTGGCCCCAGTGCTGCAATGATACCGCGAGACCCACGCTCACCGGCTCCAGA

TTTATCAGCAATAAACCAGCCAGCCGGAAGGGCCGAGCGCAGAAGTGGTCCTGCAACTTTATCCGCCTCC

ATCCAGTCTATTAATTGTTGCCGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGCTTCATTCAGCTCCGGTTCCCA

ACGATCAAGGCGAGTTACATGATCCCCCATGTTGTGCAAAAAAGCGGTTAGCTCCTTCGGTCCTCCGATC

GTTGTCAGAAGTAAGTTGGCCGCAGTGTTATCACTCATGGTTATGGCAGCACTGCATAATTCTCTTACTG

TCATGCCATCCGTAAGATGCTTTTCTGTGACTGGTGAGTACTCAACCAAGTCATTCTGAGAATAGTGTAT

GCGGCGACCGAGTTGCTCTTGCCCGGCGTCAATACGGGATAATACCGCGCCACATAGCAGAACTTTAAAA

GTGCTCATCATTGGAAAACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAAATGTTGAATACTCATACTC

TTCCTTTTTCAATATTATTGAAGCATTTATCAGGGTTATTGTCTCATGAGCGGATACATATTTGAATGTA

TTTAGAAAAATAAACAAATAGGGGTTCCGCGCACATTTCCCCGAAAAGTGCCACCTGTATGCGGTGTGAA

ATACCGCACAGATGCGTAAGGAGAAAATACCGCATCAGGAAATTGTAAGCGTTAATAATTCAGAAGAACT

CGTCAAGAAGGCGATAGAAGGCGATGCGCTGCGAATCGGGAGCGGCGATACCGTAAAGCACGAGGAAGCG

GTCAGCCCATTCGCCGCCAAGCTCTTCAGCAATATCACGGGTAGCCAACGCTATGTCCTGATAGCGGTCC

GCCACACCCAGCCGGCCACAGTCGATGAATCCAGAAAAGCGGCCATTTTCCACCATGATATTCGGCAAGC

AGGCATCGCCATGGGTCACGACGAGATCCTCGCCGTCGGGCATGCTCGCCTTGAGCCTGGCGAACAGTTC

GGCTGGCGCGAGCCCCTGATGCTCTTCGTCCAGATCATCCTGATCGACAAGACCGGCTTCCATCCGAGTA

CGTGCTCGCTCGATGCGATGTTTCGCTTGGTGGTCGAATGGGCAGGTAGCCGGATCAAGCGTATGCAGCC

GCCGCATTGCATCAGCCATGATGGATACTTTCTCGGCAGGAGCAAGGTGAGATGACAGGAGATCCTGCCC

CGGCACTTCGCCCAATAGCAGCCAGTCCCTTCCCGCTTCAGTGACAACGTCGAGCACAGCTGCGCAAGGA

ACGCCCGTCGTGGCCAGCCACGATAGCCGCGCTGCCTCGTCTTGCAGTTCATTCAGGGCACCGGACAGGT

CGGTCTTGACAAAAAGAACCGGGCGCCCCTGCGCTGACAGCCGGAACACGGCGGCATCAGAGCAGCCGAT

TGTCTGTTGTGCCCAGTCATAGCCGAATAGCCTCTCCACCCAAGCGGCCGGAGAACCTGCGTGCAATCCA

TCTTGTTCAATCATGCGAAACGATCCTCATCCTGTCTCTTGATCAGAGCTTGATCCCCTGCGCCATCAGA

TCCTTGGCGGCGAGAAAGCCATCCAGTTTACTTTGCAGGGCTTCCCAACCTTACCAGAGGGCGCCCCAGC

TGGCAATTCCGGTTCGCTTGCTGTCCATAAAACCGCCCAGTCTAGCTATCGCCATGTAAGCCCACTGCAA

GCTACCTGCTTTCTCTTTGCGCTTGCGTTTTCCCTTGTCCAGATAGCCCAGTAGCTGACATTCATCCGGG

GTCAGCACCGTTTCTGCGGACTGGCTTTCTACGTGAAAAGGATCTAGGTGAAGATCCTTTTTGATAATCT

CATGCCTGACATTTATATTCCCCAGAACATCAGGTTAATGGCGTTTTTGATGTCATTTTCGCGGTGGCTG

AGATCAGCCACTTCTTCCCCGATAACGGAGACCGGCACACTGGCCATATCGGTGGTCATCATGCGCCAGC

TTTCATCCCCGATATGCACCACCGGGTAAAGTTCACGGGAGACTTTATCTGACAGCAGACG
```

Sequence of pEQC-B: (SeqID No. 18)
(Bold = primer sequence; underlined = probe sequence)

```
TGCACTGGCCAGGGGATCACCATCCGTCGCCCCGGCGTGTCAATAATATCACTCTGTACATCCACAAAC

AGACGATAACGGCTCTCTCTTTTATAGGTGTAAACCTTAAACTGCCGTACGTATAGGCTGCGCAACTGTT

GGGAAGGGCGATCGGTGCGGGCCTCTTCGCTATTACGCCAGCTGGCGAAAGGGGGATGTGCTGCAAGGCG

ATTAAGTTGGGTAACGCCAGGGTTTTCCCAGTCACGACGTTGTAAAACGACGGCCAGTGAATTGTAATAC

GACTCACTATAGGGCGAATTGAATTTAGCGGCCGCGAATTCGCCCTTATATTTATCAATCATGGCGGGTT
```

-continued

```
TCTAGAATGTATTGGCATTAAGCCTACAAAACACACTCCTATAATATACAAATATGACCTCAACCCGTAA

ATTCCAACAAAAAACTAACCCATCCAAACTAAGCTATTCCTTAAATAACAGTGCTCAACAGTTAAGAAGG

GGCTAATCCATTTTAGTAATTAAAAATAAAGGTAAAGCCAATAACATAAATTGGGGCAAATACAAAGATG

GCTCTTAGCAAAGTCAAGTTAAATGATACATTAAATAAGGATCAGCTGCTGTCATCTAGCAAATACACTA

TTCAACGTAGTACAGGAGATAATATTGACACTCCCAATTATGATGTGCAAAAACACTTAAACAAACTATG

TGGTATGCTATTAATCACTGAAGATGCAAATCATAAATTCACAGGATTAATAGGTATGTTATATGCTATG

TCCAGGTTAGGAAGGGAAGACACTATAAAGATACTTAAAGATGCTGGATATCATGTTAAAGCTAATGGAG

TAGATATAACAACATATCGTCAAGATATAAATGGAAAGGAAATGAAATTCGAAGTATTAACATTATCAAG

CTTGACATCAGAAATACAAGTCAATATTGAGATAGAATCTAGAAAGTCCTACAAAAAAATGCTAAAAGAG

ATGGGAGAAGTGGCTCCAGAATATAGGCATGATTCTCCAGACTGTGGGATGATAATACTGTGTATAGCTG

CACTTGTAATAACCAAATTAGCAGCAGGAGATAGATCAGGTCTTACAGCAGTAATTAGGAGGGCAAACAA

TGTCTTAAAAAACGAAATAAAACGCTACAAGGGCCTCATACCAAAGGATATAGCTAACAGTTTTTATGAA

GTGTTTGAAAAACACCCTCATCTTATAGATGTTTTTGTGCACTTTGGCATTGCACAATCATCCACAAGAG

GGGGTAGTAGAGTTGAAGGAATCTTTGCAGGATTATTTATGAATGCCTATGGTTCAGGGCAAGTAATGCT

AAGATGGGGAGTTTTAGCCAAATCTGTAAAAAATATCATGCTAGGACATGCTAGTGTCCAGGCAGAAATG

GAGCAAGTTGTGGAAGTCTATGAGTATGCACAGAAGTTGGGAGGAGAAGCTGGATTCTACCATATATTGA

ACAATCCAAAAGCATCATTGCTGTCATTAACTCAATTTCCTAACTTCTCAAGTGTGGTCCTAGGCAATGC

AGCAGGTCTAGGCATAATGGGAGAGTATAGAGGTACACCAAGAAACCAGGATCTTTATGATGCAGCCAAA

GCATATGCAGAGCAACTCAAAGAAAATGGAGTAATAAACTACAGTGTATTAGACTTAACAGCAGAAGAAT

TGGAGGCCATAAAGCATCAACTCAACCCCAAAGAAGATGATGTAGAAAGGGCGAATTCGTTTAAACCTGC

AGGACTAGTCCCTTTAGTGAGGGTTAATTCTGAGCTTGGCGTAATCATGGTCATAGCTGTTTCCTGTGTG

AAATTGTTATCCGCTCACAATTCCACACAACATACGAGCCGGAAGCATAAAGTGTAAAGCCTGGGGTGCC

TAATGAGTGAGCTAACTCACATTAATTGCGTTGCGCTCACTGCCCGCTTTCCAGTCGGGAAACCTGTCGT

GCCAGCTGCATTAATGAATCGGCCAACGCGCGGGGAGAGGCGGTTTGCGTATTGGGCGCTCTTCCGCTTC

CTCGCTCACTGACTCGCTGCGCTCGGTCGTTCGGCTGCGGCGAGCGGTATCAGCTCACTCAAAGGCGGTA

ATACGGTTATCCACAGAATCAGGGGATAACGCAGGAAAGAACATGTGAGCAAAAGGCCAGCAAAAGCCCA

GGAACCGTAAAAAGGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGTTTCCCCCTGGAAGC

TCCCTCGTGCGCTCTCCTGTTCCGACCCTGCCGCTTACCGGATACCTGTCCGCCTTTCTCCCTTCGGGAA

GCGTGGCGCTTTCTCATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTATCGTCTTGAGTCCAAC

CCGGTAAGACACGACTTATCGCCACTGGCAGCAGCCACTGGTAACAGGATTAGCAGAGCGAGGTATGTAG

GCGGTGCTACAGAGTTCTTGAAGTGGTGGCCTAACTACGGCTACACTAGAAGGACAGTATTTGGTATCTG

CGCTCTGCTGAAGCCAGTTACCTTCGGAAAAAGAGTTGGTAGCTCTTGATCCGGCAAACAAACCACCGCT

GGTAGCGGTGGTTTTTTTGTTTGCAAGCAGCAGATTACGCGCAGAAAAAAAGGATCTCAAGAAGATCCTT

TGATCTTTTCTACGGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAATCTAAAGTATATAT

GAGTAAACTTGGTCTGACAGTTACCAATGCTTAATCAGTGAGGCACCTATCTCAGCGATCTGTCTATTTC

GTTCATCCATAGTTGCCTGACTCCCCGTCGTGTAGATAACTACGATACGGGAGGGCTTACCATCTGGCCC

CAGTGCTGCAATGATACCGCGAGACCCACGCTCACCGGCTCCAGATTTATCAGCAATAAACCAGCCAGCC

GGAAGGGCCGAGCGCAGAAGTGGTCCTGCAACTTTATCCGCCTCCATCCAGTCTATTAATTGTTGCCGGG
```

-continued
```
AAGCTAGAGTAAGTAGTTCGCCAGTTAATAGTTTGCGCAACGTTGTTGCCATTGCTACAGGCATCGTGGT

GTCACGCTCGTCGTTTGGTATGGCTTCATTCAGCTCCGGTTCCCAACGATCAAGGCGAGTTACATGATCC

CCCATGTTGTGCAAAAAAGCGGTTAGCTCCTTCGGTCCTCCGATCGTTGTCAGAAGTAAGTTGGCCGCAG

TGTTATCACTCATGGTTATGGCAGCACTGCATAATTCTCTTACTGTCATGCCATCCGTAAGATGCTTTTC

TGTGACTGGTGAGTACTCAACCAAGTCATTCTGAGAATAGTGTATGCGGCGACCGAGTTGCTCTTGCCCG

GCGTCAATACGGGATAATACCGCGCCACATAGCAGAACTTTAAAAGTGCTCATCATTGGAAAACGTTCTT

CGGGGCGAAAACTCTCAAGGATCTTACCGCTGTTGAGATCCAGTTCGATGTAACCCACTCGTGCACCCAA

CTGATCTTCAGCATCTTTTACTTTCACCAGCGTTTCTGGGTGAGCAAAAACAGGAAGGCAAAATGCCGCA

AAAAAGGGAATAAGGGCGACACGGAAATGTTGAATACTCATACTCTTCCTTTTTCAATATTATTGAAGCA

TTTATCAGGGTTATTGTCTCATGAGCGGATACATATTTGAATGTATTTAGAAAAATAAACAAATAGGGGT

TCCGCGCACATTTCCCCGAAAAGTGCCACCTGTATGCGGTGTGAAATACCGCACAGATGCGTAAGGAGAA

AATACCGCATCAGGAAATTGTAAGCGTTAATAATTCAGAAGAACTCGTCAAGAAGGCGATAGAAGGCGAT

GCGCTGCGAATCGGGAGCGGCGATACCGTAAAGCACGAGGAAGCGGTCAGCCCATTCGCCGCCAAGCTCT

TCAGCAATATCACGGGTAGCCAACGCTATGTCCTGATAGCGGTCCGCCACACCCAGCCGGCCACAGTCGA

TGAATCCAGAAAAGCGGCCATTTTCCACCATGATATTCGGCAAGCAGGCATCGCCATGGGTCACGACGAG

ATCCTCGCCGTCGGGCATGCTCGCCTTGAGCCTGGCGAACAGTTCGGCTGGCGCGAGCCCCTGATGCTCT

TCGTCCAGATCATCCTGATCGACAAGACCGGCTTCCATCCGAGTACGTGCTCGCTCGATGCGATGTTTCG

CTTGGTGGTCGAATGGGCAGGTAGCCGGATCAAGCGTATGCAGCCGCCGCATTGCATCAGCCATGATGGA

TACTTTCTCGGCAGGAGCAAGGTGAGATGACAGGAGATCCTGCCCCGGCACTTCGCCCAATAGCAGCCAG

TCCCTTCCCGCTTCAGTGACAACGTCGAGCACAGCTGCGCAAGGAACGCCCGTCGTGGCCAGCCACGATA

GCCGCGCTGCCTCGTCTTGCAGTTCATTCAGGGCACCGGACAGGTCGGTCTTGACAAAAAGAACCGGGCG

CCCCTGCGCTGACAGCCGGAACACGGCGGCATCAGAGCAGCCGATTGTCTGTTGTGCCCAGTCATAGCCG

AATAGCCTCTCCACCCAAGCGGCCGGAGAACCTGCGTGCAATCCATCTTGTTCAATCATGCGAAACGATC

CTCATCCTGTCTCTTGATCAGAGCTTGATCCCCTGCGCCATCAGATCCTTGGCGGCGAGAAAGCCATCCA

GTTTACTTTGCAGGGCTTCCCAACCTTACCAGAGGGCGCCCCAGCTGGCAATTCCGGTTCGCTTGCTGTC

CATAAAACCGCCCAGTCTAGCTATCGCCATGTAAGCCCACTGCAAGCTACCTGCTTTCTCTTTGCGCTTG

CGTTTTCCCTTGTCCAGATAGCCCAGTAGCTGACATTCATCCGGGGTCAGCACCGTTTCTGCGGACTGGC

TTTCTACGTGAAAAGGATCTAGGTGAAGATCCTTTTTGATAATCTCATGCCTGACATTTATATTCCCCAG

AACATCAGGTTAATGGCGTTTTTGATGTCATTTTCGCGGTGGCTGAGATCAGCCACTTCTTCCCCGATAA

CGGAGACCGGCACACTGGCCATATCGGTGGTCATCATGCGCCAGCTTTCATCCCCGATATGCACCACCGG

GTAAAGTTCACGGGAGACTTTATCTGACAGCAGACG
```

A similar procedure as for above described EQC was worked out for the construction of the internal extraction control (IEC) for said RSV q-RT PCR assay.

Construction of the Internal Extraction Control (IEC) for the RSV q-RT PCR Assay In order to monitor the RNA extraction efficiency of the EasyMAG (BioMérieux, Boxtel, The Netherlands) internal extraction controls (IEC) were constructed This included design of the following plasmid constructs containing:

Primer sequence identical to the RSV-A selected primers with a random 'in-between' sequence. A Taqman probe containing the fluorescent dye TET or FAM will detect this sequence. This construct is labeled as internal extraction control RSV-A (pIEC-A)

Primer sequence identical to the RSV-B selected primers with a random 'in-between' sequence. A Taqman probe containing the fluorescent dye NED or FAM will detect this sequence. This construct is labeled as internal extraction control RSV-B (pIEC-B)

Primers and Probes

Figure 5B:
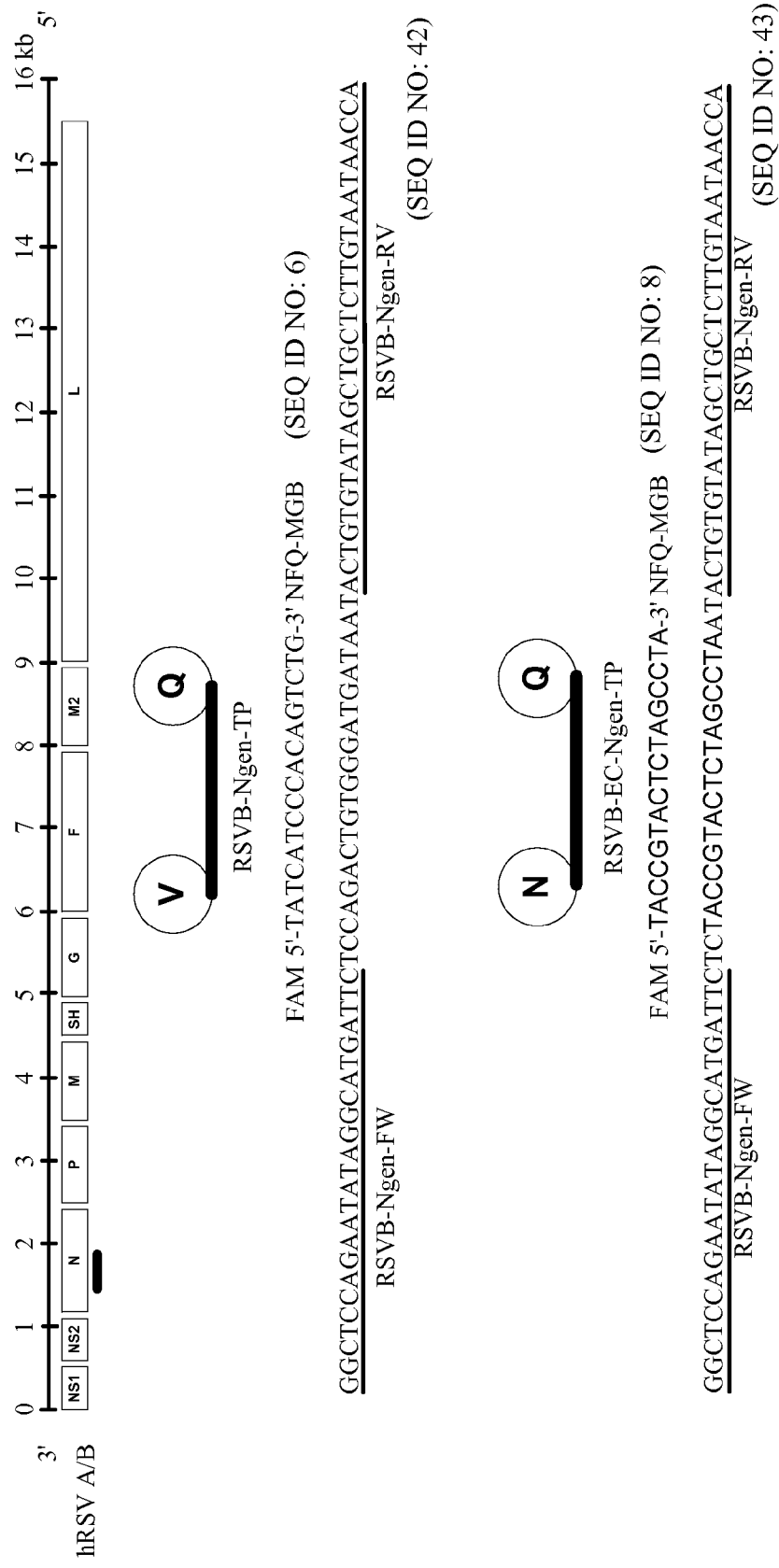

The primers ordered to generate the sequence to be cloned in pIEC-A (RSV-A-Fgen-EC-FW and RSV-A-Fgen-EC-RV) and pIEC-B (RSV-B-Ngen-EC-FW and RSV-B-Ngen-EC-RV) are described below and cover roughly one primer sequence and half of the specific probe sequence. A schematic representation of the RSV sequences and the corresponding primers and probes can be found in FIG. 5. The primers overlap partly, which enables them to anneal during a PCR amplification (see below).

| Oligonucleotide | Sequence | |
|---|---|---|
| RSV-A-Fgen-EC-FW | 5'-CTGTGATAGA GTTCCAACAA AAGAACAATG CGTATGGATT GGT-3' | SeqID No. 19 |
| RSV-A-Fgen-EC-RV | 5'-AGTTACACCT GCATTAACAC TAAATTCCCT AATGACCAAT CCA-3' | SeqID No. 20 |
| RSV-B-Ngen-EC-FW | 5'-GGCTCCAGAA TATAGGCATG ATTCTCTACC GTACTCTAGC C-3' | SeqID No. 21 |
| RSV-B-Ngen-EC-RV | 5'-TGGTTATTAC AAGTGCTGCT ATACACAGTA TTAGGCTAGA G-3' | SeqID No. 22 |

Amplification and Cloning

The complementary primer sequences (pIEC-A (RSV-A-Fgen-EC-FW and RSV-A-Fgen-EC-RV) and pIEC-B (RSV-B-Ngen-EC-FW and RSV-B-Ngen-EC-RV) were submitted to a PCR reaction forming a short piece of double stranded DNA. The PCR mixes and conditions are specified below:

| Component | Vol (µl) | # Samples 8 |
|---|---|---|
| RSV-A | | |
| Rnase free water | 39.17 | 352.53 µl |
| PCR Buffer (15 mM MgCl₂) | 5 | 45 µl |
| dNTPs | 0.4 | 3.6 µl |
| RSV-A Fgen-EC-FW | 0.5 | 4.5 µl |
| RSV-A Fgen-EC-RV | 0.5 | 4.5 µl |
| Expand ™ HF PCR | 0.43 | 3.87 µl |
| Total volume | 46 | 414 µl |
| RSV-B | | |
| Rnase free water | 39.17 | 352.53 µl |
| PCT Buffer (15 mM MgCl₂) | 5 | 45 µl |
| dNTPs | 0.4 | 3.6 µl |
| RSV-B Ngen-EC-FW | 0.5 | 4.5 µl |
| RSV-B Ngen-EC-RV | 0.5 | 4.5 µl |
| Expand ™ HF PCR | 0.43 | 3.87 µl |
| Total volume | 46 | 414 µl |

The PCR program used was 94° C. for 2 minutes followed by 35 cycles of 94° C. for 15 seconds, 54° C.-62° C. (gradient, performed on cycler 857) for 30 seconds and 68° C. for 30 seconds. A final step was performed at 68° C. for 10 minutes concluded with a final hold at 4° C.

TOPO-TA Cloning

The obtained PCR fragments were cloned using the TOPO TA cloning kit (Invitrogen, Merelbeke, Belgium) following the manufacturer's instructions. Briefly, 4 µl PCR product (without purification) was mixed with 1 µl salt solution and 1 µl vector.

The ligation reaction was transformed into TOP10 chemically competent E. coli cells following the manufacturer's instructions.

After growing the E. coli cultures overnight, 10 colonies per construct (pIEC-A and pIEC-B) were transferred to liquid LB medium, grown overnight and a miniprep (Qiagen, Hilden, Germany) was performed (total volume of 50 µl plasmid DNA (concentration not measured).

Sequencing

A total of 0.75 µl of the generated miniprep DNA was submitted to sequencing. Sequencing was done using the Big Dye Terminator (BDT) Cycle Sequencing Kit v3.1 (Cat n°. 4337457, Applied Biosystems, Calif., USA). The mix composition with a final volume of 5.75 micro liter in each well was as follows:

| Component | Volume (µl) |
|---|---|
| BDT | 0.25 |
| Water | 1.50 |
| Total volume | 5.00 |
| amplicon | 0.75 |

BDT = Big Dye Terminator

The sequencing reactions were performed using the primer set

"T3" (5'-ATTAACCCTCACTAAAGGGA-3') (Seg ID No. 15) and

"T7" (5'-TAATACGACTCACTATAGGG-3') (SeqID No. 16) which are located on the TOPO-TA vector.

The sequencing PCR was done using the 9800 Fast Thermal Cycler (Applied Biosystems (ABI), Cat. nr. 4356204, Calif., USA). The PCR conditions were 96° C. for 5 seconds, 50° C. for 5 seconds, 60° C. for 1 minute and 15 seconds and this for 25 cycles in total followed by a final hold at 12° C.

In Vitro RNA Transcription

One correct clone of each IEC construct was linearized using the restriction enzyme ApaLI (FIG. 6). Restriction enzyme digestion (ApaLI) proceeded at 37° C. for 3 hours using restriction enzyme buffer 4 and BSA. After restriction, the reactions were purified. To the restriction digest mix, 1/20 volumes of 0.5M EDTA (1 µl), 1/10 volumes of NaOAC (2 µl) and 2 volumes of EtOH (40 µl) were added. The mixture was placed at −20° C. for minimum 15 minutes, and then spun for 15 minutes at maximum speed. The supernatant was discarded and the pellet was dissolved in 50 µl TE buffer. These purified templates were then transcribed using the MEGAshortscript™ T7 Kit (Ambion, Cat. nr. 1354, Tex., USA. The reaction mixtures were incubated at 37° C. for 4 hours. After incubation at 37° C. the reaction mixtures were put at 4° C. The total length of the transcribed RNA is predicted to be 1100 nucleotides.

DNA Removal

The transcription mixtures were treated with TURBO DNase™ (2 µl added to transcription mix, Ambion, Cat. Nr. 2238, Tex., USA). The DNase treatment lasted for 1 hour at 37° C. in a final volume of 100 µl. The RNA was purified by means of an RNA extraction on the EasyMAG (BioMérieux) eluting in 100 µl.

Real-time IEC Quantification

The purified transcripts were diluted 1/1000 and submitted to a real-time PCR quantification either in the presence or the absence of the RT enzyme. The compositions of the various mixes are depicted below.

The amplification program used on the ABI9700 HT real-time PCR equipment was 48° C. for 30 minutes, 95° C. for 10 minutes followed by 45 cycles of 95° C. for 15 seconds and 60° C. for 1 minute.

| | | Reaction Vol. (µl) 25 | | | |
|---|---|---|---|---|---|
| | | Concentration | | Volume for (µl) | |
| Mix item | Unit | Stock | Final | 1 sample | X samples |
| Rnase free water | | | | 0.325 | 7.15 |
| Yeast tRNA | ng/ml | 10000 | 120 | 0.300 | 6.60 |
| 2x Master Mix w/o UNGr | X | 2.00 | 1.000 | 12.500 | 275.00 |
| 40X MultiScribe and Rnase Inhibitor Mix | X | 40.00 | 0.013 | 0.625 | 13.75 |
| Probe IEC-B | µM | 5.00 | 0.100 | 0.500 | 11.00 |
| primer 1 | µM | 20.00 | 0.300 | 0.375 | 8.25 |
| primer 2 | µM | 20.00 | 0.300 | 0.375 | 8.25 |
| | | Total Volume Mix (µl) | | | 330.00 |
| | | Volume Mix/Tube (µl) | | 15.00 | |
| | | Total RNA | | 10.00 | |

Sample Processing, an Example

In total 5 clinical samples were processed Each clinical sample was diluted in PBS/1% DTT to a final volume of 2.2 ml. This mix was processed on the AFA (Covaris) for 60 seconds prior to the addition of 4 ml lysis buffer (EasyMAG, BioMérieux). From these 6.2 ml per sample, 3 ml was processed on the EasyMAG (BioMérieux) and the RNA was eluted in 110 µl of which 10 µl was processed in the q-RT-PCR in duplicate. The experiment was repeated once starting from extraction with the remaining 3 ml.

Aliquoting and Storage of IEC

A total of 24 negative samples (PBS, 10% DTT, 1 ml final volume) were lysed with 2 ml Lysis buffer (BioMérieux) and incubated for 10 minutes. Three aliquots of IEC-B (110 µl) were defrosted and diluted with buffer 3 (440 µl, BioMérieux). A total of 550 µl magnetic silica beads (BioMérieux) were added to this IEC dilution and all three mixes were pooled to obtain a final volume of 3300 µl IEC/magnetic silica beads mix. This mix was diluted as described for the IEC addition of the EasyQ (BioMérieux), i.e., 125 µl mix was dispensed in 24 wells (using the pre-programmed protocol "2" on the automatic dispensing pipet of BioMérieux) and of this total mix, 100 µl was added to each sample, using the pre-programmed protocol "3" on the automatic dispensing pipet of BioMérieux. The IEC were further extracted on the EasyMAG and eluted in 110 µl. From this mix 10 µl was submitted to a q-RT-PCR amplification.

Results

PCR

The amplicon for the RSV-A internal extraction control construct had a size of 77 base pairs while the amplicon for the RSV-B internal extraction control construct had a size of 74 base pairs. These PCR amplified fragments were ligated in a TOPO-TA vector and transformed into competent E. coli. The transformants were grown overnight on solid LB/ampicillin plates. A total of 10 colonies were transferred to liquid LB/Ampicillin medium and again grown overnight. A miniprep (Qiagen, Hilden, Germany) was prepared from these cultures and the resulting DNA was submitted to sequencing.

Sequencing

As expected, not all PCR fragments were ligated in the same direction in the TOPO-TA vector. The RSV-A internal extraction control PCR fragments in clones 5, 8 and 10 were ligated in the correct orientation. This was also the case for clones 1, 3, 7 and 8 for the RSV-B internal extraction control.

In Vitro Transcription

Clone 5 (pIEC-A) and clone 1 (pIEC-B) were submitted to a restriction digest using ApaLI and purified as described above. The linearized and purified constructs were submitted to an in vitro transcription (using the MEGAshortscript™ T7 Kit (Ambion)). The residual DNA was removed using the TURBO DNase™ (Ambion). The transcripts were purified by means of an RNA extraction on the EasyMAG (BioMérieux) as described above.

Real-time PCR Results

The pure transcripts were diluted ¹/₁₀₀₀ and submitted to a real-time PCR quantification reaction with and without RT enzyme to determine the residual DNA content of the transcripts. For IEC-A, the signal generated in the presence of reverse transcriptase (RT) emerged at Ct 8 while in the absence of the RT enzyme the signal only emerged at Ct 30-31. For IEC-B this was respectively Ct 8 (+RT) and Ct 30 (−RT). Hence both IECs had a difference of 22 cycles between the signal with and without RT. This corresponds to a difference of more than 6 logs (22/3.3=6.6), indicating 1 residual DNA molecule for $10^6$ RNA molecules. This is acceptable to use as an RNA control. The IEC RNA was diluted 1000 000 times (estimated Ct value 27.4 for IEC-A and 27.6 for IEC-B), aliquoted in 90 µl aliquots and stored at −80° C.

Analysis of Clinical Samples, an Example

In this experiment, five clinical samples were processed Since all assays were run in monoplex, only one IEC was needed.

Standard Curves

In the standard curves for EQC-A the slope was −3.34, with a Y-axis intercept of 42.43 and a linear range of 7 logs.

For EQC-B the slope was −3.34, with a Y-axis intercept of 41.23 and a linear range of 7 logs.

IEC

When looking at the IEC signals it could be observed that all signals emerged above the noise at the same moment, around Ct 28. This experiment was repeated once starting from extraction (Hence an independent addition of IEC-B to the samples during this extraction), resulting in comparable values. All values were combined and plotted. The average of all measurements of the IEC-B was 28.09, with a standard deviation of 0.36.

Sample Analysis

⅗samples produced a signal for RSV-A: sputum 17.38 and 17.68, "NPW 4" 21.74 and 22.15 and "NPW 6" 24.61 and 25.60. No signal was detected for NPW 3 and NPW 5 on the RSV-A analysis plate. These samples did produce an RSV-B signal: "NPW 3" 21.63 and 22.15 and "NPW 5" 25.49 and 25.58.

CONCLUSION

Two vectors were constructed and sequenced. They both contained a unique sequence covering either the RSV-A or RSV-B specific primers and a unique sequence in between the two primer sequences that can anneal with a unique fluorescent probe. The purified DNase-treated transcripts were analyzed in the presence or the absence of the RT enzyme in a real-time PCR quantification assay. This indicated that for both IECs a suited RNA control transcript was obtained that contained less than 1 DNA molecule in 1 000 000 RNA molecules, covering the 2 log difference specified as an acceptance criteria.

The IEC-B was diluted 1 000 000 times and added to clinical samples during their extraction on the EasyMAG. This process was repeated during a second, independent analysis of the samples. This experiment revealed comparable signals emerging around Ct 28.09, with a standard deviation of 0.36, regardless of the RSV RNA present in the sample (subtype A or B).

The IEC-B was aliquoted and stored in 110 μl aliquots in −80° C. The repeated testing of these aliquots revealed a Ct value of 26.32 when the threshold was set at 0.02.

The sequence of pIEC-A (clone 5) and pIEC-B (clone 1) respectively are depicted below:

```
Sequence of pIEC-A (SeqID No. 23):
(Bold = primer sequence; underlined = probe sequence)
TGCACTGGCCAGGGGGATCACCATCCGTCGCCCCGGCGTGTCAATAATATCACTCTGTACATCCACAAAC

AGACGATAACGGCTCTCTCTTTTATAGGTGTAAACCTTAAACTGCCGTACGTATAGGCTGCGCAACTGTT

GGGAAGGGCGATCGGTGCGGGCCTCTTCGCTATTACGCCAGCTGGCGAAAGGGGATGTGCTGCAAGGCG

ATTAAGTTGGGTAACGCCAGGGTTTTCCCAGTCACGACGTTGTAAAACGACGGCCAGTGAATTGTAATAC

GACTCACTATAGGGCGAATTGAATTTAGCGGCCGCGAATTCGCCCTTCTGTGATAGAGTTCCAACAAAAG

AACAATGCGTATGGATTGGTCATTAGGGAATTTAGTGTTAATGCAGGTGTAACTAAGGGCGAATTCGTTT

AAACCTGCAGGACTAGTCCCTTTAGTGAGGGTTAATTCTGAGCTTGGCGTAATCATGGTCATAGCTGTTT

CCTGTGTGAAATTGTTATCCGCTCACAATTCCACACAACATACGAGCCGGAAGCATAAAGTGTAAAGCCT

GGGGTGCCTAATGAGTGAGCTAACTCACATTAATTGCGTTGCGCTCACTGCCCGCTTTCCAGTCGGGAAA

CCTGTCGTGCCAGCTGCATTAATGAATCGGCCAACGCGCGGGGAGAGGCGGTTTGCGTATTGGGCGCTCT

TCCGCTTCCTCGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAAAAGGCCAGCA

AAAGCCCAGGAACCGTAAAAAGGCCGCGTTGCTGGCGTTTTTCCATAGGCTCCGCCCCCCTGACGAGCAT

CACAAAAATCGACGCTCAAGTCAGAGGTGGCGAAACCCGACAGGACTATAAAGATACCAGGCGTTTCCCC

CTGGAAGCTCCCTCGTGCGCTCTCCTGTTCCGACCCTGCCGCTTACCGGATACCTGTCCGCCTTTCTCCC

TTCGGGAAGCGTGGCGCTTTCTCATAGCTCACGCTGTAGGTATCTCAGTTCGGTGTAGGTCGTTCGCTCC

AAGCTGGGCTGTGTGCACGAACCCCCCGTTCAGCCCGACCGCTGCGCCTTATCCGGTAACTATCGTCTTG

AGTCCAACCCGGTAAGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAGAAGGACAGTATTT

GGTATCTGCGCTCTGCTGAAGCCAGTTACCTTCGGAAAAAGAGTTGGTAGCTCTTGATCCGGCAAACAAA

CCACCGCTGGTAGCGGTGGTTTTTTTGTTTGCAAGCAGCAGATTACGCGCAGAAAAAAAGGATCTCAAGA

AGATCCTTTGATCTTTTCTACGGGGTCTGACGCTCAGTGGAACGAAAACTCACGTTAAGGGATTTTGGTC

ATGAGATTATCAAAAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCTATCTCAGCGATCTG

TCTATTTCGTTCATCCATAGTTGCCTGACTCCCCGTCGTGTAGATAACTACGATACGGGAGGGCTTACCA

TCTGGCCCCAGTGCTGCAATGATACCGCGAGACCCACGCTCACCGGCTCCAGATTTATCAGCAATAAACC

AGCCAGCCGGAAGGGCCGAGCGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACGTTGTTGCCATTGCTACAGGC

ATCGTGGTGTCACGCTCGTCGTTTGGTATGGCTTCATTCAGCTCCGGTTCCCAACGATCAAGGCGAGTTA

CATGATCCCCCATGTTGTGCAAAAAAGCGGTTAGCTCCTTCGGTCCTCCGATCGTTGTCAGAAGTAAGTT
```

-continued

GGCCGCAGTGTTATCACTCATGGTTATGGCAGCACTGCATAATTCTCTTACTGTCATGCCATCCGTAAGA

TGCTTTTCTGTGACTGGTGAGTACTCAACCAAGTCATTCTGAGAATAGTGTATGCGGCGACCGAGTTGCT

CTTGCCCGGCGTCAATACGGGATAATACCGCGCCACATAGCAGAACTTTAAAAGTGCTCATCATTGGAAA

ACGTTCTTCGGGGCGAAAACTCTCAAGGATCTTACCGCTGTTGAGATCCAGTTCGATGTAACCCACTCGT

GCACCCAACTGATCTTCAGCATCTTTTACTTTCACCAGCGTTTCTGGGTGAGCAAAAACAGGAAGGCAAA

ATGCCGCAAAAAAGGGAATAAGGGCGACACGGAAATGTTGAATACTCATACTCTTCCTTTTTCAATATTA

TTGAAGCATTTATCAGGGTTATTGTCTCATGAGCGGATACATATTTGAATGTATTTAGAAAAATAAACAA

ATAGGGGTTCCGCGCACATTTCCCCGAAAAGTGCCACCTGTATGCGGTGTGAAATACCGCACAGATGCGT

AAGGAGAAAATACCGCATCAGGAAATTGTAAGCGTTAATAATTCAGAAGAACTCGTCAAGAAGGCGATAG

AAGGCGATGCGCTGCGAATCGGGAGCGGCGATACCGTAAAGCACGAGGAAGCGGTCAGCCCATTCGCCGC

CAAGCTCTTCAGCAATATCACGGGTAGCCAACGCTATGTCCTGATAGCGGTCCGCCACACCCAGCCGGCC

ACAGTCGATGAATCCAGAAAAGCGGCCATTTTCCACCATGATATTCGGCAAGCAGGCATCGCCATGGGTC

ACGACGAGATCCTCGCCGTCGGGCATGCTCGCCTTGAGCCTGGCGAACAGTTCGGCTGGCGCGAGCCCCT

GATGCTCTTCGTCCAGATCATCCTGATCGACAAGACCGGCTTCCATCCGAGTACGTGCTCGCTCGATGCG

ATGTTTCGCTTGGTGGTCGAATGGGCAGGTAGCCGGATCAAGCGTATGCAGCCGCCGCATTGCATCAGCC

ATGATGGATACTTTCTCGGCAGGAGCAAGGTGAGATGACAGGAGATCCTGCCCCGGCACTTCGCCCAATA

GCAGCCAGTCCCTTCCCGCTTCAGTGACAACGTCGAGCACAGCTGCGCAAGGAACGCCCGTCGTGGCCAG

CCACGATAGCCGCGCTGCCTCGTCTTGCAGTTCATTCAGGGCACCGGACAGGTCGGTCTTGACAAAAGA

ACCGGGCGCCCCTGCGCTGACAGCCGGAACACGGCGGCATCAGAGCAGCCGATTGTCTGTTGTGCCCAGT

CATAGCCGAATAGCCTCTCCACCCAAGCGGCCGGAGAACCTGCGTGCAATCCATCTTGTTCAATCATGCG

AAACGATCCTCATCCTGTCTCTTGATCAGAGCTTGATCCCCTGCGCCATCAGATCCTTGGCGGCGAGAAA

GCCATCCAGTTTACTTTGCAGGGCTTCCCAACCTTACCAGAGGGCGCCCCAGCTGGCAATTCCGGTTCGC

TTGCTGTCCATAAAACCGCCCAGTCTAGCTATCGCCATGTAAGCCCACTGCAAGCTACCTGCTTTCTCTT

TGCGCTTGCGTTTTCCCTTGTCCAGATAGCCCAGTAGCTGACATTCATCCGGGGTCAGCACCGTTTCTGC

GGACTGGCTTTCTACGTGAAAAGGATCTAGGTGAAGATCCTTTTTGATAATCTCATGCCTGACATTTATA

TTCCCCAGAACATCAGGTTAATGGCGTTTTTGATGTCATTTTCGCGGTGGCTGAGATCAGCCACTTCTTC

CCCGATAACGGAGACCGGCACACTGGCCATATCGGTGGTCATCATGCGCCAGCTTTCATCCCCGATATGC

ACCACCGGGTAAAGTTCACGGGAGACTTTATCTGACAGCAGACG

Sequence of pIEC-B (SeqID No. 24):
(Bold = primer sequence; Underlined = probe sequence)
TGCACTGGCCAGGGGGATCACCATCCGTCGCCCCGGCGTGTCAATAATATCACTCTGTACATCCACAAAC

AGACGATAACGGCTCTCTCTTTTATAGGTGTAAACCTTAAACTGCCGTACGTATAGGCTGCGCAACTGTT

GGGAAGGGCGATCGGTGCGGGCCTCTTCGCTATTACGCCAGCTGGCGAAAGGGGGATGTGCTGCAAGGCG

ATTAAGTTGGGTAACGCCAGGGTTTTCCCAGTCACGACGTTGTAAAACGACGGCCAGTGAATTGTAATAC

GACTCACTATAGGGCGAATTGAATTTAGCGGCCGCGAATTCGCCCTTGGCTCCAGAATATAGGCATGATT

CTC<u>TACCGTACTCTAGCCTAAT</u>ACTGTGTATAGCAGCACTTGTAATAACCAAAGGGCGAATTCGTTTAAA

CCTGCAGGACTAGTCCCTTTAGTGAGGGTTAATTCTGAGCTTGGCGTAATCATGGTCATAGCTGTTTCCT

GTGTGAAATTGTTATCCGCTCACAATTCCACACAACATACGAGCCGGAAGCATAAAGTGTAAAGCCTGGG

GTGCCTAATGAGTGAGCTAACTCACATTAATTGCGTTGCGCTCACTGCCCGCTTTCCAGTCGGGAAACCT

GTCGTGCCAGCTGCATTAATGAATCGGCCAACGCGCGGGGAGAGGCGGTTTGCGTATTGGGCGCTCTTCC

GCTTCCTCGCTCACTGACTCGCTGCGCTCGGTCGTTCGGCTGCGGCGAGCGGTATCAGCTCACTCAAAGG

CGGTAATACGGTTATCCACAGAATCAGGGGATAACGCAGGAAAGAACATGTGAGCAAAAGGCCAGCAAAA

-continued

```
GCCCAGGAACCGTAAAAAGGCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCACGTTAAGGGATTTTGGTCATG
AGATTATCAAAAAGGATCTTCACCTAGATCCTTTTAAATTAAAAATGAAGTTTTAAATCAATCTAAAGTA
TATATGAGTAAACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGGCTTACCATCT
GGCCCCAGTGCTGCAATGATACCGCGAGACCCACGCTCACCGGCTCCAGATTTATCAGCAATAAACCAGC
CAGCCGGAAGGGCCGAGCGCAGAAGTGGTCCTGCAACTTTATCCGCCTCCATCCAGTCTATTAATTGTTG
CCGGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTGCTCTT
GCCCGGCGTCAATACGGGATAATACCGCGCCACATAGCAGAACTTTAAAAGTGCTCATCATTGGAAAACG
TTCTTCGGGGCGAAAACTCTCAAGGATCTTACCGCTGTTGAGATCCAGTTCGATGTAACCCACTCGTGCA
CCCAACTGATCTTCAGCATCTTTTACTTTCACCAGCGTTTCTGGGTGAGCAAAAACAGGAAGGCAAAATG
CCGCAAAAAAGGGAATAAGGGCGACACGGAAATGTTGAATACTCATACTCTTCCTTTTTCAATATTATTG
AAGCATTTATCAGGGTTATTGTCTCATGAGCGGATACATATTTGAATGTATTTAGAAAAATAAACAAATA
GGGGTTCCGCGCACATTTCCCCGAAAAGTGCCACCTGTATGCGGTGTGAAATACCGCACAGATGCGTAAG
GAGAAAATACCGCATCAGGAAATTGTAAGCGTTAATAATTCAGAAGAACTCGTCAAGAAGGCGATAGAAG
GCGATGCGCTGCGAATCGGGAGCGGCGATACCGTAAAGCACGAGGAAGCGGTCAGCCCATTCGCCGCCAA
GCTCTTCAGCAATATCACGGGTAGCCAACGCTATGTCCTGATAGCGGTCCGCCACACCCAGCCGGCCACA
GTCGATGAATCCAGAAAAGCGGCCATTTTCCACCATGATATTCGGCAAGCAGGCATCGCCATGGGTCACG
ACGAGATCCTCGCCGTCGGGCATGCTCGCCTTGAGCCTGGCGAACAGTTCGGCTGGCGCGAGCCCCTGAT
GCTCTTCGTCCAGATCATCCTGATCGACAAGACCGGCTTCCATCCGAGTACGTGCTCGCTCGATGCGATG
TTTCGCTTGGTGGTCGAATGGGCAGGTAGCCGGATCAAGCGTATGCAGCCGCCGCATTGCATCAGCCATG
ATGGATACTTTCTCGGCAGGAGCAAGGTGAGATGACAGGAGATCCTGCCCCGGCACTTCGCCCAATAGCA
GCCAGTCCCTTCCCGCTTCAGTGACAACGTCGAGCACAGCTGCGCAAGGAACGCCCGTCGTGGCCAGCCA
CGATAGCCGCGCTGCCTCGTCTTGCAGTTCATTCAGGGCACCGGACAGGTCGGTCTTGACAAAAAGAACC
GGGCGCCCCTGCGCTGACAGCCGGAACACGGCGGCATCAGAGCAGCCGATTGTCTGTTGTGCCCAGTCAT
AGCCGAATAGCCTCTCCACCCAAGCGGCCGGAGAACCTGCGTGCAATCCATCTTGTTCAATCATGCGAAA
CGATCCTCATCCTGTCTCTTGATCAGAGCTTGATCCCCTGCGCCATCAGATCCTTGGCGGCGAGAAAGCC
ATCCAGTTTACTTTGCAGGGCTTCCCAACCTTACCAGAGGGCGCCCCAGCTGGCAATTCCGGTTCGCTTG
CTGTCCATAAAACCGCCCAGTCTAGCTATCGCCATGTAAGCCCACTGCAAGCTACCTGCTTTCTCTTTGC
```

-continued

GCTTGCGTTTTCCCTTGTCCAGATAGCCCAGTAGCTGACATTCATCCGGGTCAGCACCGTTTCTGCGGA

CTGGCTTTCTACGTGAAAAGGATCTAGGTGAAGATCCTTTTTGATAATCTCATGCCTGACATTTATATTC

CCCAGAACATCAGGTTAATGGCGTTTTTGATGTCATTTTCGCGGTGGCTGAGATCAGCCACTTCTTCCCC

GATAACGGAGACCGGCACACTGGCCATATCGGTGGTCATCATGCGCCAGCTTTCATCCCCGATATGCACC

ACCGGGTAAAGTTCACGGGAGACTTTATCTGACAGCAGACG (B) Use of MNAzymes for the Quantification of RSV-A and RSV-B Viral Strains and a Control Nucleic Acid Sequences Via Triplex Real Time PCR A triplex PCR assay, which used three MNAzymes to facilitate real time monitoring, was developed for the simultaneous detection and quantification of (i) RSV-A (F gene sequences), (ii) RSV-B (N gene sequences) and (iii) an internal extraction control (IEC B) sequence. The RSV-A primers and partzymes, which targeted a region of the F gene, were designed to be fully complementary to the RSV-A sequence but to contain several base mismatches in the corresponding region of the RSV-B genome. Similarly, the RSV-B primers and partzymes, which targeted a region in N gene, were designed to be fully complementary to the RSV-B sequence but to contain several base mismatches in the corresponding region of the RSV-A genome.

.1 Partzyme Oligonucleotides for a Triplex RT-PCR Assay

Multiple targets can be simultaneously detected in one multiplexed reaction that comprises multiple unique MNAzymes. Each MNAzyme has sensor arms specific for one target and substrate arms specific for a unique member of a series of generic reporter substrates, each one of which is labeled with a different fluorophore.

In the following example, two MNAzymes were designed to detect two strains of RSV from clinical samples with a third MNAzyme designed to detect a synthetic control sequence, which was applied to the sample prior to nucleic acid extraction.

TABLE 2

| SEQ ID # | Target | Partzyme Name | Partzyme sequence listed in 5' to 3' direction (P = phosphate group) |
|---|---|---|---|
| 25 | RSVA | RSVAA5/2-P | CAGACTACTAGAGATTACCATACAACGAGAGGAAACCTT-P |
| 26 | RSVA | RSVAB6/2-P | TGCCCAGGGAGGCTAGCGGGAATTTAGTGTTAATGCA-P |
| 27 | RSVB | RSVBA5/3-P | AGACTGTGGGATGATAATACTACAACGAGGTTGTGCTG-P |
| 28 | RSVB | RSVBB6/3-P | CGGTTGGTGAGGCTAGCTGTGTATAGCTGCACTTGTA-P |
| 29 | IEC B | IEC3A5/6-P | ACCTGCAGGACTAGTCCCTTTACAACGAGAGGCGTGAT-P |
| 30 | IEC B | IEC3B6/6-P | CTGGGAGGAAGGCTAGCTAGTGAGGGTTAATTCTGAG-P |

.2 Reporter Substrates

In this example, three different reporter substrates, each labeled with a different fluorophore, were used. The sequences of the substrates are written 5' to 3' below. In the current example, a first substrate SubBi-2 was end-labeled with a 6-FAM moiety at the 5' end and a BHQ1 moiety at the 3' end and was designated SubBi-2-FB. The substrate SubBi-2-FB was used to monitor the accumulation of RSVA amplicons. The cleavage of SubBi-2-FB was monitored at 516 nm with excitation at 492 nm. A second substrate SubBi-3 was end-labeled with a 6-JOE moiety at the 5' end and a BHQ1 moiety at the 3' end and was designated SubBi-3-JB. The substrate SubBi-3-JB was used to follow the amplification of the region of the RSVB and SubBi-3-JB cleavage was monitored at 555 nm with excitation at 535 nm. The third substrate SubBi-6 was end-labeled with a Quasar 670 moiety at the 5' end and a BHQ2 moiety at the 3' end and was designated SubBi-6-Q6B2. The substrate SubBi-6-Q6B2 was used to monitor the amplification of the internal extraction control (IEC B) and cleavage of SubBi-3-Q6B2 was monitored at 665 nm with excitation at 635 nm. The sequences of the three substrates are listed below. The lower case bases represent RNA and the upper case bases represent DNA. The moieties at the 5' and 3' ends are indicated.

TABLE 3

| SEQ. ID No. | Substrate sequence listed in 5' to 3' direction | Name |
|---|---|---|
| 31 | (FAM)AAGGTTTCCTCguCCCTGGGCA(BHQ1) | SubBi-2-FB |
| 32 | (JOE)CAGCACAACCguCACCAACCG(BHQ1) | SubBi-3-JB |
| 33 | (Q670)ATCACGCCTCguTCCTCCCAG(BHQ2) | SubBi-6-Q6B2 |

.3. PCR Primers for Amplification of the Target Sequences

The primers 5RSVA/3 and 3RSVA/3 were used for the amplification of RSVA F gene sequence. The primers 5RSVB/3 and 3RSVB/3 were used to amplify the RSVB N gene sequence. The primers 51ECB/1 and 31ECA3/3 were used to amplify the Internal extraction control (IECB) sequence. The sequences of the oligonucleotide PCR primers are listed below.

TABLE 4

| SEQ. ID No. | Primer sequence listed in 5' to 3' direction | Name |
|---|---|---|
| 34 | GTGATAGAGTTCCAACAAAAGA | 5RSVA/3 |
| 35 | AAGTGCTTACAGGTGTAGTTA | 3RSVA/3 |
| 36 | GCTCCAGAATATAGGCATGAT | 5RSVB/3 |

TABLE 4-continued

| SEQ. ID No. | Primer sequence listed in 5' to 3' direction | Name |
|---|---|---|
| 37 | GATCTATCTCCTGCTGCTAAT | 3RSVB/3 |
| 38 | CTTGTAATAACCAAAGGGCGA | 5IECB/1 |
| 39 | GGAAACAGCTATGACCATGATT | 3IECA3/3 |

.4. Reaction Components: Amplification and Quantification of Target Sequences

Reverse transcription, real time amplification and quantification of the target sequences were performed in a total reaction volume of 25 µL. All reactions were conducted on an Mx3005P™ QPCR System (Stratagene). The cycling parameters were 50° C. for 30 minutes (reverse transcription step), followed by 95° C. for 7 minutes, then 10 cycles of 95° C. for 15 seconds and initially 65° C. for 30 seconds with a 1° C. decrease in temperature per cycle to 55° C., and finally 50 cycles of 95° C. for 15 seconds and 50° C. for 120 seconds. The reactions contained 40 nM of 5RSVA/3, 40 nM of 5RSVB/3, 40 nM of 51ECB/1, 200 nM of 3RSVA/3, 200 nM of 3RSVB/3, 200 nM of 31ECA3/3, 200 nM of each substrate (SubBi-2-FB, SubBi-3-JB and SubBi-6-Q6B2), 8 mM MgCl$_2$, 200 µM of each dNTP, 10 units Rnasin (Promega), 1× Immobuffer (Bioline) 1 unit of 1 mmolase (Bioline) and 40U of M-MLV(—H) (Promega). Each duplicate reaction contained a dilution of both RSVA and RSVB genomic RNA along with an RNA preparation of a T7 Transcription of the IECB sequence, or no template nucleic acid.

Two standard curves were produced, each performed in duplicate. The first standard curve was generated by performing four fold dilutions of both RSVA viral genomic RNA and the T7 transcript of the IECB through a constant concentration of background of RSVB viral genomic RNA. The second standard curve was generated by performing four fold dilutions of both RSVB viral RNA and the T7 transcript of the IECB through a constant concentration of background RSVA genomic RNA.

TABLE 5

RSVA/IECB Standard curves

| | Threshold (Ct) | | |
|---|---|---|---|
| | RSVA (FAM) | RSVB (JOE) | IECB (Quasar 670) |
| Standard 1 | 22.9 | 19.6 | 11.6 |
| Standard 2 | 25.3 | 19.9 | 13.8 |
| Standard 3 | 28.1 | 20.4 | 15.9 |
| Standard 4 | 30.6 | 20.4 | 19.0 |
| Standard 5 | 32.9 | 20.3 | 20.8 |
| Standard 6 | 36.4 | 20.6 | 23.4 |
| Water only (no template control) | No Ct | No Ct | No Ct |
| Standard Curve | $R^2$ = 0.995 Slope = −4.102 Efficiency = 75.2% | N/A | $R^2$ = 0.997 Slope = −3.954 Efficiency = 79% |

TABLE 6

RSVB/IECB Standard curves

| | Threshold (Ct) | | |
|---|---|---|---|
| | RSVA (FAM) | RSVB (JOE) | IECB (Quasar 670) |
| Standard 1 | 26.7 | 15.4 | 11.2 |
| Standard 2 | 27.1 | 17.6 | 13.7 |
| Standard 3 | 27.3 | 20.0 | 16.3 |
| Standard 4 | 27.4 | 22.4 | 18.6 |
| Standard 5 | 27.4 | 25.3 | 21.1 |
| Standard 6 | 27.3 | 28.3 | 22.2 |
| Water only (no template control) | No Ct | No Ct | No Ct |
| Standard Curve | N/A | $R^2$ = 0.996 Slope = −4.276 Efficiency = 71.3% | $R^2$ = 0.989 Slope = −3.771 Efficiency = 84.2% |

Each calibration dilution series produced a standard curve that had a high correlation coefficient ($\geq 0.989$), and high specificity indicated by the lack of background in no template controls. Further, the fact that the threshold cycle (Ct) for RSVB remained relatively constant (varying by $\leq 1$ Ct value) in reactions, where there was a constant input amount of RSVB but varying amounts of RSVA, indicates the specificity of the primer and substrate systems for the specific viral strains being quantified.

The suitability of the real time MNAzyme assay for the detection and quantification of RSVA and RSVB was further tested by analysing human specimens. RNA extracted from sputum and/or nasopharyngeal washes was analysed and RSVA and/or RSVB was detected in several samples.

Results of the Comparison Between Method A (=q-RT PCR Technology) and Method B (=MNAzyme Technology)

TABLE 7

Analysis of sputum and nasopharyngeal washes using Method A and Method B respectively.

| | Data (Cts) Method B | | | Data (Cts) Method A | | Method B Results | | Method A Results | |
|---|---|---|---|---|---|---|---|---|---|
| Sample | RSVA | RSVB | IECB | RSVA | RSVB | RSVA | RSVB | RSVA | RSVB |
| Sputum 36 | 15.6/17.1 | ND × 2r | 30/27.3 | 21.2 | ND | + | − | + | − |
| NPW 10 | 19.7/20.2 | ND × 2r | 28.2 | 25.0 | ND | + | − | + | − |
| NPW 11 | 34.4/36.0 | 23.2/24.0 | 29.1 | 39.8 | 22.4 | + | + | + | + |
| NPW 12 | 37.1/39.3 | 25.1/26.3 | 28.3 | 42.5 | 24.0 | + | + | + | + |
| NPW 13 | ND × 2r | 27.2/39 | 28.8 | ND | 25.1 | − | + | − | + |
| NPW 14 | 18.9/19.5 | ND × 2r | ND | 24.3 | ND | + | − | + | − |
| NPW 15 | 18.4/18.9 | ND × 2r | 28.5 | 23.5 | ND | + | − | + | − |
| NPW 16 | ND/41.7 | 26.1/26.8 | 27.8 | 43.6 | 24.7 | + 1/4 | + | + | + |
| NPW 17 | 38/37 | ND × 2r | 28.2 | ND | 40.7 | + | − | − | + |
| NPW 18 | ND × 2r | 14.2/15.3 | 26.4 | ND | 15.1 | − | + | − | + |

TABLE 7-continued

Analysis of sputum and nasopharyngeal washes using Method A and Method B respectively.

| | | | | | | | | | |
|---|---|---|---|---|---|---|---|---|---|
| NPW 19 | 37.1/ND | 21.1/21.7 | 28.7 | ND | 20.8 | + 1/4 | + | − | + |
| NPW 20 | ND/41.4 | 19.7/20.0 | 27.5 | ND | 19.6 | + 1/4 | + | − | + |
| NPW 21 | 19.2/20.1 | ND × 2r | 29.1 | 23.7 | ND | + | − | + | − |
| NPW 22 | 41.8/ND | ND × 2r | 28.6 | ND | 30.3 | + 1/4 | − | − | + |
| NPW 23 | 38.3/36.4 | 23.5/23.8 | 28.3 | ND | 22.7 | + 3/4 | + | − | + |
| NPW 24 | 40.6/ND | 34.5/ND | 27.9 | ND | 30.7 | + 1/4 | + 1/4 | − | + |
| NPW 25 | 30.7/34.3 | ND × 2r | 28.5 | 34.8 | 42.5 | + | − | + | + |
| NPW 26 | 18.6/19.3 | ND × 2r | 28.2 | 22.9 | ND | + | − | + | − |
| NPW 27 | ND × 2r | 19.0/20.1 | 27.7 | ND | 19.6 | − | + | − | + |
| NPW 30 | 18.1/19.2 | ND × 2r | 28.2 | 23.4 | ND | + | − | + | − |
| NPW 32 | ND × 2r | 25.1/26.3 | 29.1 | ND | 24.3 | − | + | − | + |
| NPW 33 | 15.2 | ND | 28.4 | 20.2 | ND | + | − | + | − |
| NPW 34 | 21.4 | ND | 27.8 | 25.7 | ND | + | − | + | − |
| NPW 36 | 19.4 | ND | 27.7 | 24.3 | ND | + | − | + | − |
| NPW 37 | ND | 19.5 | 28.6 | ND | 20.7 | − | + | − | + |
| NPW 38 | 17.1 | ND | ND | 21.8 | 42.0 | + | − | + | + |
| NPW 39 | 36.7 | 21.5 | 27.3 | 40.6 | 21.2 | + | + | + | + |
| Sputum 1 | 27.2/29.6 | 15.0/14.2 | ND | 35.4 | 15.8 | + | + | + | + |
| Sputum 2 | 22.8/25.1 | 15.2/14.0 | ND | 28.0 | 15.5 | + | + | + | + |

| | Method B | | Method A | | | Method B Results | | Method A Results | |
|---|---|---|---|---|---|---|---|---|---|
| Sample | RSVA | RSVB | RSVA | RSVB | | RSVA | RSVB | RSVA | RSVB |
| Sputum 3 | 27.5/29.2 | ND × 2r | NA | 17.4 | NA | − | + | − | + | − |
| NPW 6 | 25.4/26.5 | ND × 2r | 38.0 | − | 22.9 | 21.6 | + | − | + | + |
| NPW 7 | 23.8/25.1 | ND × 2r | 25.9 | 21.7 | − | − | + | − | + | − |
| NPW 8 | 23.7/25.6 | ND × 2r | NA | − | NA | 25.5 | + | − | − | + |
| NPW 9 | 26.8/28.7 | ND × 2r | 26.1 | 24.6 | − | − | + | − | + | − |

Ct = threshold cycle/positive signal; ND = not detected; + = positive result; − = negative result.

Up to four (4) replicates of each sample were analyzed and when only some were detectable the number of positive per total number of replicates analyzed is indicated (e.g. 1 in 4=1/4).

When sufficient material was present each sample was analyzed in duplicate twice (i.e. duplicates in 2 separate runs).

The results in the Table show that there is high concordance between the two methods (A and B) used in terms of Ct value (threshold cycle value).

The invention claimed is:

1. A method for identifying, detecting or quantifying the presence of at least one target Respiratory Syncytial Virus (RSV) nucleic acid in a sample, comprising the following steps:
   (a) providing two or more oligonucleotide components having the ability to anneal to the target RSV nucleic acid, wherein a first oligonucleotide component and a second oligonucleotide component are capable of forming a catalytically active multi-component nucleic acid enzyme (MNAzyme) once annealed to the target RSV nucleic acid;
   (b) contacting said two or more oligonucleotide components with said sample wherein said sample permits the binding of said at least one target RSV nucleic acid to said two or more oligonucleotide components and formation of the MNAzyme;
   (c) contacting the MNAzyme with a catalyzable nucleic acid reporter substrate that is separate from the at least one target RSV nucleic acid; and
   (d) identifying, detecting or quantifying the presence of the target RSV nucleic acid by detecting catalysis of the nucleic acid reporter substrate.

2. The method according to claim 1, wherein the viral load of RSV in said sample is determined by quantifying the catalytic products produced by the MNAzyme.

3. The method of claim 1, wherein the catalytic activity of the MNAzyme comprises cleavage of a nucleic acid reporter substrate.

4. The method of claim 3, wherein the nucleic acid reporter substrate is labeled.

5. The method of claim 4, wherein detection of the label is enhanced following cleavage of the nucleic acid reporter substrate.

6. The method of claim 4, wherein the label is a fluorophore.

* * * * *